(12) United States Patent
Flaumenhaft et al.

(10) Patent No.: US 12,235,278 B2
(45) Date of Patent: Feb. 25, 2025

(54) COMPOSITIONS AND METHODS FOR EVALUATION OF ANTIPLATELET DRUG SENSITIVITY

(71) Applicant: Beth Israel Deaconess Medical Center, Inc., Boston, MA (US)

(72) Inventors: Robert Flaumenhaft, Boston, MA (US); David Barrios, Brighton, MA (US); Secil Koseoglu, Somerville, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1016 days.

(21) Appl. No.: 17/270,830

(22) PCT Filed: Aug. 23, 2019

(86) PCT No.: PCT/US2019/047901
§ 371 (c)(1),
(2) Date: Feb. 23, 2021

(87) PCT Pub. No.: WO2020/041698
PCT Pub. Date: Feb. 27, 2020

(65) Prior Publication Data
US 2021/0181214 A1 Jun. 17, 2021

Related U.S. Application Data

(60) Provisional application No. 62/722,378, filed on Aug. 24, 2018.

(51) Int. Cl.
*G01N 33/86* (2006.01)
*G01N 33/68* (2006.01)
(52) U.S. Cl.
CPC ......... *G01N 33/86* (2013.01); *G01N 33/6803* (2013.01); *G01N 2800/52* (2013.01)
(58) Field of Classification Search
CPC .............................. G01N 33/86; G01N 33/53
See application file for complete search history.

(56) References Cited

U.S. PATENT DOCUMENTS 6,391,568 B1 5/2002 Schneider et al.

FOREIGN PATENT DOCUMENTS

WO WO 2010/060918 A1 6/2010
WO WO 2014/025685 A2 2/2014

OTHER PUBLICATIONS

PCT/US2019/047901, Nov. 15, 2019, International Search Report and Written Opinion.
PCT/US2019/047901, Mar. 11, 2021, International Preliminary Report on Patentability.
International Search Report and Written Opinion for PCT/US2019/047901, mailed on Nov. 15, 2019.
International Preliminary Report on Patentability for PCT/US2019/047901, mailed on Mar. 11, 2021.
Bo et al., Calmodulin-dependent protein kinase II (CaMKII) mediates radiation-induced mitochondrial fission by regulating the phosphorylation of dynamin-related protein 1 (Drp1) at serine 616. Biochem Biophys Res Commun. Jan. 8, 2018;495(2):1601-1607. doi: 10.1016/j.bbrc.2017.12.012. Epub Dec. 5, 2017. PMID: 29217195.
Koseoglu et al., Dynamin-related protein-1 controls fusion pore dynamics during platelet granule exocytosis. Arterioscler Thromb Vasc Biol. Mar. 2013;33(3):481-8. doi: 10.1161/ATVBAHA.112.255737. Epub Jan. 3, 2013. PMID: 23288151; PMCID: PMC3573216.
Zheng et al., Phosphorylation of dynamin-related protein 1 at Ser616 regulates mitochondrial fission and is involved in mitochondrial calcium uniporter-mediated neutrophil polarization and chemotaxis. Mol Immunol. Jul. 2017;87:23-32. doi: 10.1016/j.molimm.2017.03.019. Epub Apr. 4, 2017. PMID: 28388446.

*Primary Examiner* — Prema M Mertz
(74) *Attorney, Agent, or Firm* — Wolf, Greenfield & Sacks, P.C.

(57) ABSTRACT

In some aspects, the disclosure relates to compositions and methods for detecting phosphorylation of dynamin-related protein 1 (Dip1) at position Ser-616. In some embodiments, methods described by the disclosure are useful for detecting antiplatelet agent sensitivity in a subject. In some embodiments, methods described by the disclosure are useful for detecting if a subject has been previously exposed to an antiplatelet agent.

17 Claims, 13 Drawing Sheets

Specification includes a Sequence Listing.

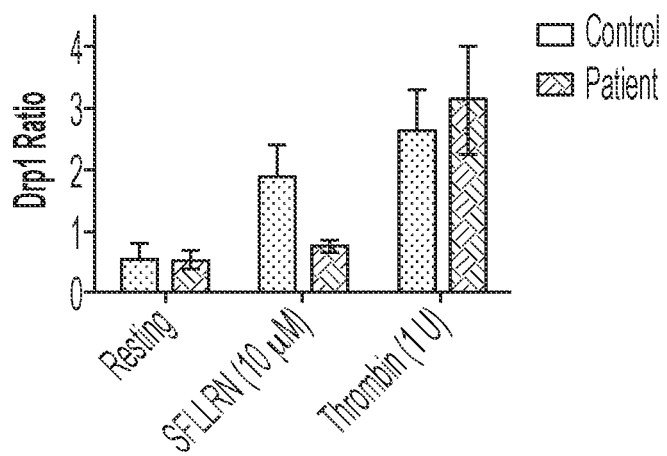
FIG. 7A
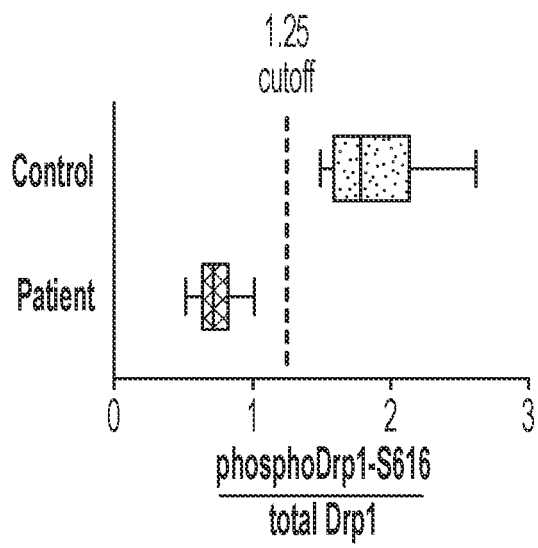
FIG. 7B
| cutoff 1.25 | Control | Patient |
|---|---|---|
| pDrp1-Ser616 | TP - 6 | FP - 0 |
| lack of pDrp1-Ser616 | FN - 0 | TN - 13 |
FIG. 7C

COMPOSITIONS AND METHODS FOR EVALUATION OF ANTIPLATELET DRUG SENSITIVITY

RELATED APPLICATIONS

This application is a national stage filing under 35 U.S.C. § 371 of International PCT Application PCT/US2019/047901, filed Aug. 23, 2019, which claims priority under 35 U.S.C. § 119 (e) to U.S. Provisional Application, U.S. Ser. No. 62/722,378, filed on Aug. 24, 2018, the entire contents of each are incorporated herein by reference.

FEDERALLY SPONSORED RESEARCH

This invention was made with government support under grant number HL112809, awarded by the National Institutes of Health. The government has certain rights in the invention.

BACKGROUND

Dynamin related protein 1 (Drp1) is a GTPase of the dynamin superfamily that functions in membrane remodeling. Drp1 has been observed to function in mitochondrial fusion and to have a broader function in membrane remodeling. Typically, Drp1 functions as a mechanoenzyme, and its assembly facilitates membrane tubulation and constriction. In a mouse model of thrombus formation, inhibition of Drp1 blocked platelet accumulation at sites of vascular injury.

Platelet Drp1 is phosphorylated in an activation-dependent manner. Phosphorylation of Drp1 at Serine 616 (also referred to as Ser616 and S616) promotes mitochondrial fission caused by assemblage of Drp1 into a constrictive ring that pinches the mitochondria. In contrast, phosphorylation of Drp1 at Serine 637 (also referred to as Ser637 and S637) inhibits assembly of Drp1, preventing mitochondrial fission. Kinases involved in platelet Drp1 phosphorylation have not previously been evaluated.

The gold standard for platelet function testing is platelet aggregometry, which is fundamentally unchanged since its development 50 years ago. The approach is expensive and time-consuming, typically requiring scheduling, 1.5 h of technician time, and interpretation from a trained pathologist. Thus, there is an unmet need for an inexpensive, platelet function assay that can rapidly quantify the degree to which a patient's antiplatelet therapy is active.

SUMMARY

Dynamin-related protein 1 (Drp1) belongs to the dynamin superfamily of mechanoenzymes that function in mitochondrial fission and fusion. Inhibition of platelet Drp1 typically blocks granule exocytosis and thrombus formation. Platelet Drp1 is phosphorylated at Ser616 and Ser637, and phosphorylation at these two sites differentially affects Drp1 activity.

The disclosure is based, in part, on the recognition that platelet activation with certain agonists results in phosphorylation of Drp1 at Ser616, but not at Ser637. As described further in the Examples section, it was observed that PAR1-mediated phosphorylation of Ser616 is under the control of MAPK p38 and ERK1/2, while Ser637 is phosphorylated by protein kinase A (PKA). Unexpectedly, these two signaling pathways are connected via negative feedback. The PKA-dependent Ser637 pathway must be turned off to permit phosphorylation at Ser616. Downregulation of PKA in response to certain agonists is accomplished by release of ADP from platelet dense granule stores and subsequent activation of $P2Y_{12}$.

One advantage of methods described herein compared to currently available platelet functional assays is the ability of Drp1-Ser616 assay to detect the inhibition of platelets by multiple antiplatelet agents. As described further in the Examples section, assay methods described herein are, in some embodiments, able to detect a subject's sensitivity to certain antiplatelet agents, for example, clopidogrel, cangrelor, prasugrel, ticagrelor, ticlopidine, aspirin, cilostazol, dipyridamole, vorapaxar, and terutroban. Thus, in some embodiments, methods described by the disclosure are useful as point-of-care (POC) assays to determine a subject's sensitivity to antiplatelet therapies and/or whether a subject has previously been exposed to one or more antiplatelet therapies.

Accordingly, the disclosure relates, in some aspects, to methods for determining antiplatelet drug (e.g., aspirin, clopidogrel, vorapaxar, etc.) sensitivity in a subject using a phosphorylated Drp1-Ser616 (phosphoDrp1-Ser616) assay. Without wishing to be bound by any particular theory, detecting the absence of phospho-Drp1-Ser616 (or a decreased ratio of phospho-Drp1-Ser616:phospho-Drp1-Ser637) in a biological sample indicates that a subject is sensitive to treatment with certain antiplatelet agents (e.g., platelet antagonists or inhibitors, such as clopidogrel, vorapaxar, aspirin, etc.). Conversely, the presence of phospho-Drp1-Ser616 in a biological sample, in some embodiments, indicates that a subject is not sensitive (e.g., may be resistant) to treatment with certain antiplatelet agents. In some embodiments, methods described by the disclosure are performed in vitro.

Methods described by the disclosure are also useful, in some embodiments, for determining whether a subject has impaired platelet function. In some embodiments, the methods comprise detecting in a biological sample obtained from a subject the presence or absence of a Dynamin-related protein 1 (Drp1) that is phosphorylated at position Ser616 (phospho-Drp1-Ser616). In some embodiments, a biological sample has been stimulated (e.g., stimulated prior to detecting the presence or absence of phospho-Drp1-Ser616) with a platelet agonist, arachidonic acid, protease-activated receptor 1 (PAR1) peptide agonist (such as a SFLLRN (SEQ ID NO: 1) peptide), thromboxane (TP) receptor agonist (such as U46619).

In some embodiments, a biological sample is contacted with an agent that binds specifically to a Drp1 protein with a phosphorylated serine at position 616 (phospho-Drp1-Ser616). In some embodiments, the absence of phospho-Drp1-Ser616 in a biological sample (e.g., following stimulation by a platelet agonist, such as arachidonic acid, ADP, SFLLRN (SEQ ID NO: 1), AYPGKF (SEQ ID NO: 2), or U46619) is indicative of impaired platelet function in the subject from which the biological sample was obtained.

The disclosure is based, in part, on detecting the presence or absence of phospho-Drp1-Ser616 to determine whether the activity of certain platelet receptors (e.g., $P2Y_{12}$) is inhibited or antagonized in a subject having or suspected of having impaired platelet function. In some embodiments, impaired platelet function is indicative of inhibition of a $P2Y_{12}$ receptor in a subject. In some embodiments, impaired platelet function is indicative of inhibition of a cyclooxygenase (COX) in a subject. In some embodiments, impaired platelet function is indicative of inhibition of PDE3A phosphodiesterase in a subject. In some embodiments, impaired platelet function is indicative of inhibition of PAR1 in a subject. In some embodiments, impaired platelet function is indicative of inhibition of a TP receptor in the subject.

In some embodiments, a biological sample has been stimulated (e.g., with a platelet agonist, such as arachidonic acid, ADP, SFLLRN (SEQ ID NO: 1), AYPGKF (SEQ ID NO: 2) or U46619) prior to contacting the sample with an agent that binds specifically to phospho-Drp1-Ser616.

Surgeons are generally reluctant to perform surgery on patients receiving antiplatelet therapy, so in some cases they may require discontinuation of antiplatelet medications before surgery. Yet, the time that a patient must discontinue antiplatelet drugs prior to surgery is poorly defined and varies substantially among patients owing to differences in metabolism. Thus, in some aspects, methods described by the disclosure are useful for determining whether a subject has previously been exposed to an antiplatelet agent, or whether a platelet agent that has been ingested by a subject is still active in the subject.

In some embodiments, the reduction of the ratio of phospho-Drp1-Ser616 to total Drp1(e.g., the absence of phospho-Drp1-Ser616) in a sample indicates that the subject from which the sample was obtained has been previously exposed to clopidogrel, cangrelor, prasugrel, ticagrelor, ticlopidine, and/or other antiplatelet agents. In some embodiments, previous exposure to clopidogrel, cangrelor, prasugrel, ticagrelor, ticlopidine, and/or other antiplatelet agents results in inhibition of a $P2Y_{12}$ receptor.

In some embodiments, the absence of phospho-Drp1-Ser616 in the sample indicates that the subject has been previously exposed to aspirin and/or a non-steroidal anti-inflammatory drug (NSAID) and/or a cyclooxygenase (COX) inhibitor. In some embodiments, previous exposure to aspirin and/or NSAIDs results in inhibition of a cyclooxygenase (COX).

In some embodiments, the absence of phospho-Drp1-Ser616 in the sample indicates that the subject has been previously exposed to cilostazol and/or a phosphodiesterase inhibitor, for example dipyridamole. In some embodiments, previous exposure to cilostazol and/or dipyridamole results in inhibition of a phosphodiesterase (e.g., PDE3A).

In some embodiments, the absence of phospho-Drp1-Ser616 in the sample indicates that the subject has been previously exposed to vorapaxar. In some embodiments, previous exposure to vorapaxar results in inhibition of PAR1.

In some embodiments, the absence of phospho-Drp1-Ser616 in the sample is indicates that the subject has been previously exposed to terutroban. In some embodiments, previous exposure to terutroban results in inhibition of a TP receptor.

The disclosure is based, in part, on methods of detecting the presence or absence of phospho-Drp1-Ser616 in a biological sample that has not been subjected to cell lysis (e.g., whole blood). In some embodiments, the biological sample is whole blood. The skilled artisan recognizes, however, that methods described by the disclosure are also useful for biological samples obtained from lysates or obtained from other preparative techniques, for example, platelet rich plasma (PRP) or purified platelets.

Methods described by the disclosure may be performed on a biological sample obtained from a subject. In some embodiments, a subject is a mammal, for example a human, mouse, rat, dog, cat, or hamster. In some embodiments, a subject has or is suspected of having a cardiovascular disease or disorder or a cerebrovascular disease or disorder.

In some embodiments, a subject is a candidate for (e.g., is about to undergo) a surgical or other medical procedure.

In some embodiments, a subject has or is suspected of having a disease or disorder selected from atherosclerotic disease, coronary artery disease, stable angina, coronary bypass surgery, stroke, thrombosis or thromboembolism, peripheral arterial disease, myocardial ischemia, myocardial infarction, atrial fibrillation (AF), aneurysm, pain, fever, inflammation, heparin-induced thrombocytopenia, Hermansky-Pudlak syndrome, Gray Platelet Syndrome, and impaired platelet function due to myelodysplastic syndrome.

In some aspects, methods described by the disclosure comprise a step of contacting a biological sample with an agent that binds specifically to phospho-Drp1-Ser616. In some embodiments, an agent that binds specifically to phospho-Drp1-Ser616 is an antibody (e.g., a monoclonal antibody, a polyclonal antibody, etc.) or fragment thereof, single chain antibody (scFv), peptide, aptamer, or small molecule.

In some embodiments, an agent that binds specifically to phospho-Drp1-Ser616 does not bind to phospho-Drp1-Ser637. In some embodiments, an agent that binds specifically to phospho-Drp1-Ser616 does not bind to non-phosphorylated Drp1. In some embodiments, an agent that binds specifically to phospho-Drp1-Ser637 does not bind to phospho-Drp1-Ser616. In some embodiments, an agent that binds specifically to phospho-Drp1-Ser637 does not bind to non-phosphorylated Drp1. In some embodiments, an antibody that specifically binds to non-phosphorylated Drp1 does not bind to a phosphorylated Drp1.

In some embodiments, contact between a biological sample and an agent results in formation of a complex comprising a phospho-Drp1-Ser616 bound to the agent. In some embodiments, a detectable marker is bound to the complex and detected. In some embodiments, the presence of a detectable marker indicates the presence of phospho-Drp1-Ser616 in the sample.

In some embodiments, a detectable marker comprises a secondary reagent that binds to an agent of a complex (e.g., an agent that is bound to a phospho-Drp1-Ser616). In some embodiments, a secondary reagent is an antibody (e.g., a monoclonal antibody, polyclonal antibody, etc.), single chain antibody (scFv), peptide or peptide fragment, aptamer, or small molecule. In some embodiments, a secondary agent is conjugated to a particle, for example a polymeric particle (e.g., latex particle, etc.), a metal particle (e.g., a gold nanoparticle, magnetic nanoparticle, etc.), or a detectable moiety (e.g., a fluorescent moiety, luminescent moiety, a phosphorescent moiety, a radiolabeled moiety, a detectable enzyme, etc.).

The disclosure is based, in part, on methods of detecting phospho-Drp1-Ser616 in a biological sample that are useful in a point-of-care (POC) diagnostic. Thus, in some embodiments, obtaining a blood sample and detecting the presence or absence of phospho-Drp1-Ser616 are performed in the same location (e.g., a hospital or a physician's office). In some embodiments, the steps of obtaining a biological sample and detecting the presence or absence of phospho-Drp1-Ser616 are performed at different locations. For example, in some embodiments, a biological sample is obtained from a subject at a first location (e.g., a physician's office or hospital), and the presence or absence of phospho-Drp1-Ser616 is detected at a second location that is not the same as the first location (e.g., a central laboratory).

Typically, the presence or absence of phospho-Drp1-Ser616 is detected by a binding assay. In some embodiments, detecting is performed by ELISA, electro-chemiluminescence immunoassay, automated immunoanalyzer assay, or electrical impedance spectroscopy.

Certain aspects of the disclosure relate to methods for detecting the presence or absence of phospho-Drp1-Ser616 in a biological sample for the purpose of determining a therapeutic regimen for the subject from which the sample was obtained. In some aspects, the disclosure relates to a method for treating a subject with an antiplatelet agent. In some embodiments, the subject has previously been administered an antiplatelet agent selected from a $P2Y_{12}$-targeted antiplatelet agent, a cyclooxygenase-targeted antiplatelet agent, a PDE3A-targeted antiplatelet agent, and a PAR1-targeted antiplatelet agent, the method comprising the steps of determining whether a platelet receptor or cyclooxygenase has been inhibited in the subject by using a method of detecting the presence or absence of phospho-Drp1-Ser616 in the sample and administering to the subject an antiplatelet agent based upon the presence or absence of phospho-Drp1-Ser616 in the sample.

In some embodiments, the absence of phospho-Drp1-Ser616 protein in the biological sample is indicative of platelet responsiveness to the antiplatelet agent in the subject. In some embodiments, the presence of phospho-Drp1-Ser616 protein in the biological sample is indicative of lack of platelet responsiveness to the antiplatelet agent in the subject.

In some embodiments, a subject is administered
- a different $P2Y_{12}$-targeted agent selected from clopidogrel, cangrelor, prasugrel, ticagrelor, and ticlopidine if phospho-Drp1-Ser616 is present, and the subject has been administered a $P2Y_{12}$-targeted antiplatelet agent;
- an increased (e.g., doubling) dose of aspirin or NSAID if phospho-Drp1-Ser616 is present, and the subject has been administered a cyclooxygenase-targeted antiplatelet agent;
- an increased (e.g., doubling) dose of cilostazol or dipyridamole if phospho-Drp1-Ser616 is present, and the subject has been administered a PDE3A-targeted antiplatelet agent; or
- a non-PAR1-targeted antiplatelet agent if phospho-Drp1-Ser616 is present, and the subject has been administered a PAR1 antiplatelet agent.

In some embodiments, a subject has been administered or is suspected of having been administered an antiplatelet agent, and requires an invasive procedure. In some embodiments, the invasive procedure is delayed if the assay detects the presence of phospho-Drp1-Ser616 in a phospho-Drp1-Ser616:total Drp1 ratio below 1.25.

In some embodiments, methods of detecting the presence or absence of phospho-Drp1-Ser616 are performed on multiple biological samples obtained from a subject over a period of time (e.g., longitudinal measurements). In some embodiments, the periods of time during which biological samples are obtained and tested occur at least once per hour (e.g., 1, 2, 3, 4, 5, or more times per hour), at least once per day (e.g., 1, 2, 3, 4, 5, 6, 7, 8, 9, 10, or more times in a day), at least once per week (e.g., 1, 2, 3, 4, 5, or more times per week), at least once per month (e.g., 1, 2, 3, 4, 5, 6, 7, 8, 9, 10, or more times per month), or at least once per year (e.g., 1, 2, 3, 4, 5, or more times per year). In some embodiments, surgery is performed on the subject if the absence of phospho-Drp1-Ser616 is detected.

The disclosure is based, in part, on methods of treating a coagulopathy in a subject. In some aspects, the disclosure relates to a method for treating a subject having a coagulopathy, the method comprising the steps of: determining whether a subject has impaired platelet function by detecting the presence or absence of phospho-Drp1-Ser616 in a biological sample obtained from the subject, and administering to the subject functional platelets or desmopressin (DDAVP) based upon the absence of phospho-Drp1-Ser616 in the sample.

In some embodiments, a subject having a coagulopathy has or is suspected of having a renal disease, liver disease, or congenital platelet defect.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

Definitions

The terms "Dynamin-related protein 1" and "Drp1", as used herein, refer to a GTPase protein that is encoded by the DNM1L gene, or a variant thereof. In some embodiments, a Drp1 protein is a wild-type Drp1 protein and is encoded by the amino acid sequence represented by NCBI Accession No. NP_036192.2, NP_001265392.1, NP_005681.2, NP_001317309.1, NP_001265394.1, NP_001265393.1, NP_036193.2, or NP_001265395.1. In some embodiments, a Drp1 protein is a Drp1 isoform 1 protein and is represented by the sequence set forth in NCBI Accession No.: NP_036192. In some embodiments, a Drp1 protein is a variant of a Drp1 protein. For example, the amino acid sequence of a Drp1 protein variant may comprise one or more mutations (e.g., substitutions) relative to a wild-type Drp1 protein. In some embodiments, a Drp1 protein variant comprises one or more amino acid truncations (e.g., 1, 2, 3, 4, 5, 6, 7, 8, 9, 10, 20, 30, 40, 50, 100, etc. truncations) relative to a wild-type Drp1 protein. In some embodiments, a Drp1 protein comprises an amino acid sequence that is at least 75%, at least 85%, at least 90%, at least 95%, or at least 99% identical (e.g., as measured by a Clustal Sequence Alignment) to a wild-type Drp1 protein. In some embodiments, a Drp1 protein is phosphorylated. In some embodiments, a Drp1 protein is phosphorylated at position Serine 616 (Ser616) and is referred to as phospho-Drp1-Ser616. In some embodiments, a Drp1 protein is phosphorylated at position Serine 637 (Ser637) and is referred to as phospho-Drp1-Ser637.

A "subject" includes, but is not limited to, humans (i.e., a male or female of any age group, e.g., a pediatric subject (e.g., infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals, such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal. In certain embodiments, the subject is a human.

As used herein, the term "biological sample" refers to a specimen obtained from the tissue or cells of an organism. Examples of biological samples include, but are not limited to, organs, tissues, cells, bodily fluids (e.g. blood, urine, sweat), and genetic material (e.g. DNA). In some embodiments, a biological sample is whole blood, platelet rich plasma (PRP), or purified platelets.

A "condition," "disease," and "disorder" are used interchangeably herein. As used herein, and unless otherwise specified, the terms "treat," "treating," and "treatment" contemplate an action that occurs while a subject is suffering from the specified disease or condition, which reduces the severity of the disease or condition, or retards or slows the progression of the disease or condition ("therapeutic treatment"), and also contemplates an action that occurs before a subject begins to suffer from the specified disease or condition ("prophylactic treatment").

A "cardiovascular disease or disorder", as used herein, refers to a disease, condition or disorder that adversely affects the heart and/or blood vessels of a subject. Examples of cardiovascular disease include but are not limited to coronary artery diseases (CAD), angina, myocardial infarction, stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, atherosclerosis, embolism, and venous thrombosis. In some embodiments, a subject having a cardiovascular disease has been diagnosed by a medical professional (e.g., a doctor, such as a cardiologist) based upon the results of a physical examination, and/or the results of one or more diagnostic tests, (for example, a genetic test, electrocardiogram (ECG) screening, myocardial perfusion imaging, cardiac stress testing, etc.), and/or the determination that the subject is characterized by one or more risk factors including, but not limited to, obesity, high cholesterol, smoking tobacco, physical inactivity, etc.

A "cerebrovascular disease or disorder", as used herein, refers to a disease, condition, or disorder that adversely affects the affect the blood vessels of the brain and the cerebral circulation of a subject. Examples of cerebrovascular disease include arteriovenous malformations, germinal matrix hemorrhage, CADASIL (cerebral autosomal-dominant arteriopathy with subcortical infarcts and leukoencephalopathy), aneurysms, and arterial dissections. In some embodiments, a subject having a cerebrovascular disease has been diagnosed by a medical professional (e.g., a doctor, such as a cardiologist) based upon the results of a physical examination, and/or the results of one or more diagnostic tests (for example, a genetic test, diagnostic imaging, such as MRI or CT Scan, neurological examination, etc.), and/or the determination that the subject is characterized by one or more risk factors including, but not limited to, obesity, diabetes, high cholesterol, smoking tobacco, physical inactivity, etc.

As used herein, "impaired platelet function" refers to platelets that are functionally deficient, for example, that do not aggregate, do not form a hemostatic plug, or are deficient in thromboxane synthesis (e.g., synthesize less or no thromboxane relative to a subject who does not have impaired platelet function). Impaired platelet function can be measured by any suitable method, for example a platelet aggregometer, flow cytometer, shear-based system, or a viscoelastic test. In some embodiments, impaired platelet function occurs as a result of a genetic defect in a subject. For example, von Willebrand syndrome is typically an autosomal dominant trait which is located on the short arm p of chromosome 12 (12p13.2). In some embodiments, impaired platelet function is caused by exposure of a subject to an antiplatelet agent (e.g., previous administration of an antiplatelet agent to a subject).

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease or condition, or to delay or minimize one or more symptoms associated with the disease or condition. A therapeutically effective amount of a compound means an amount of therapeutic agent, alone or in combination with other therapies, which provides a therapeutic benefit in the treatment of the disease or condition. The term "therapeutically effective amount" can encompass an amount that improves overall therapy, reduces or avoids symptoms or causes of disease or condition, or enhances the therapeutic efficacy of another therapeutic agent. In the context of treatment of conditions associated with impaired platelet function, in certain embodiments, a therapeutically effective amount is an amount sufficient to modulate (e.g., increase or decrease) platelet count and/or platelet function (e.g., ability of platelets to aggregate or form blood clots).

As used herein a "platelet activator" or "platelet agonist" refers to a compound that can increase or induce the activity of platelets. In general, an agonist binds to a receptor (e.g., an platelet receptor, for example $P2Y_{12}$) to induce a biological response (e.g., promoting platelet activation and/or aggregation). Without wishing to be bound by any particular theory, activation of certain platelet receptors (e.g., by binding to an agonist) results in phosphorylation of Drp1-Ser616. In some embodiments, the agonist is a full agonist. A "full agonist" refers to an agonist that binds to a receptor (e.g., an aryl hydrocarbon receptor) and induces the maximum biological response that an agonist can elicit at the receptor. In some embodiments, the agonist is a partial agonist. A "partial agonist" refers to an agonist that binds to a receptor (e.g., an $P2Y_{12}$ receptor) but only induces a partial biological response compared to the biological response that a full agonist can induce, even at maximum receptor occupancy. Examples of platelet agonists (platelet activators) include arachidonic acid, thrombin, protease-activated receptor 1 (PAR1) peptide agonists (such as a SFLLRN (SEQ ID NO: 1) peptide), protease-activated receptor 4 (PAR4) peptide agonists (such as a AYPGKF (SEQ ID NO: 2) peptide), ADP, epinephrine, collagen, collagen-related protein, fibrinogen, chemokines, and thromboxane (TP) receptor agonists (such as U46619).

As used herein, an "antiplatelet agent", "platelet inhibitor" or "platelet antagonist" refers to an agent that reduces, inhibits or blocks platelet function (e.g., platelet activation and/or platelet aggregation). In some embodiments, an antiplatelet agent is an antagonist of a platelet receptor. Generally, an antagonist binds a receptor (e.g., a platelet receptor, such as $P2Y_{12}$) and inhibits signalling of that receptor. In some embodiments, an antagonist blocks the activity of platelet receptor (e.g., $P2Y_{12}$ receptor), even in the presence of a platelet agonist. Examples of antiplatelet agents include but are not limited to, ASA, also called acetylsalicylic acid or Aspirin®, Asaphen®, Entrophen®, Novasen®), clopidogrel (Plavix®), prasugrel (Effient®), ticagrelor (Brilinta®), ticlopidine, dipyridamole, cilostazol, eptifibatide (Integrillin®), tirofiban (Aggrastat®), abicximab (ReoPro®), vorapaxar (Zontivity®), forskolin, alprostadil, and terutrobin.

"Modulate," as used herein, means to decrease (e.g., inhibit, reduce, suppress) or increase (e.g., stimulate, activate, enhance) a level, response, property, activity, pathway, or process. A "modulator" is an agent capable of modulating a level, response, property, activity, pathway, or process. A modulator may be an inhibitor, antagonist, activator, or agonist. In some embodiments modulation may refer to an alteration, e.g., inhibition or increase, of the relevant level, response, property, activity, pathway, or process by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

The term "detectable label" refers to a moiety that has at least one element, isotope, or functional group incorporated into the moiety which enables detection of the molecule, e.g., a protein or peptide, or other entity, to which the label is attached. Labels can be directly attached or can be attached via a linker. It will be appreciated that the label may be attached to or incorporated into a molecule, for example, a protein, polypeptide, or other entity, at any position. In general, a detectable label can fall into any one (or more) of five classes: I) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{76}$Br, $^{99m}$Tc (Tc-$^{99}$m), $^{111}$In, $^{123}$I, $^{125}$I, $^{131}$I, $^{153}$Gd, $^{169}$Yb, and $^{186}$Re; II) a label which contains an immune moiety, which may be antibodies or antigens, which may be bound to enzymes (e.g., such as horseradish peroxidase); III) a label which is a colored, luminescent, phosphorescent, or fluorescent moieties (e.g., such as the fluorescent label fluorescein-isothiocyanate (FITC); IV) a label which has one or more photo affinity moieties; and V) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

BRIEF DESCRIPTION OF DRAWINGS

FIG. 1A shows a Western blot for Drp1 phosphorylation at Ser616 or Ser637 after treatment with SFLLRN (SEQ ID NO: 1), U46619, collagen, or forskolin. FIG. 1B shows co-localization of Drp1 or phospho-Drp1 (left) and mitochondria (middle) in resting (top) and SFLLRN-activated (SEQ ID NO: 1) (bottom) platelets. Merged image is shown on the right. FIG. 1C shows a Western blot indicating that Drp1 phosphorylation by PKA activation phosphorylates S637.

FIG. 2A shows a Western blot indicating that cilostazol prevents phophorylation at Ser616. FIG. 2B is a schematic of pathway of SFLLRN (SEQ ID NO: 1)-induced phosphorylation of Drp1 Ser616. FIG. 2C is a schematic of both Drp1 Ser616 and Ser637 phosphorylation.

FIG. 3A shows a Western blot indicating phosphorylation of Drp1 at Ser616 in the presence of a thromboxane A2 inhibitor, a P2Y$_{12}$ inhibitor, a P2Y$_1$ inhibitor, a P2X1 inhibitor, or all inhibitors. FIG. 3B is a Western blot indicating that platelet agonists fail to stimulate Drp1 phosphorylation in the presence of a P2Y$_{12}$ inhibitor. FIG. 3C is a schematic illustrating that the phosphorylation of Drp1 (S616) is P2Y$_{12}$-dependent.

FIG. 4A is a Western blot indicating that Drp1(Ser616p) formation is p38 MAP kinase-dependent. FIG. 4B is a Western blot indicating that phosphorylation of Drp1 at Ser616 occurs in platelets activated by SFLLRN (SEQ ID NO: 1), U46619, and GPVI and is p38 MAP kinase-dependent. FIGS. 4C-4G show ELISA data screening for function of other MAP kinases SFLLRN (SEQ ID NO: 1) (FIG. 4C; 10 μM); U46619 (FIG. 4D; 10 μM); collagen (FIG. 4E; 10 μg/mL); ADP (FIG. 4F; 10 μM); and AYPGKF (SEQ ID NO: 2) (FIG. 4G; 150 μM).

FIG. 5A shows a representative dose response curve for vorapaxar ([SFLLRN] (SEQ ID NO: 1)=10 μM).

FIG. 5B shows a representative dose response curve for cangrelor ([SFLLRN] (SEQ ID NO: 1)=10 μM). FIG. 5C shows a representative dose response curve for aspirin ([arachidonic acid]=10 μg/mL).

FIG. 6A shows a comparison of Drp1-Ser616 phosphorylation in response to SFLLRN (SEQ ID NO: 1) in whole blood (WB), platelet rich plasma (PRP), and twice washed platelets (2WP). FIG. 6B shows evaluation of Drp1-Ser616 phosphorylation in whole blood exposed to SFLLRN (SEQ ID NO: 1) in the presence or absence of vorapaxar, cangrelor, or p38 inhibitor, 50 μM U46619, or arachidonic acid. FIG. 6C demonstrates the stability of the phospho-Drp1-Ser616 signal following activation of platelets by SFLLRN (SEQ ID NO: 1). The signal is stable after it reaches a peak at 15 minutes.

FIGS. 7A-7C show the evaluation of clinical samples using the phospho-Drp1-Ser616-based assay. FIG. 7A shows an ELISA-based assay evaluating clinical plasma samples from patients following ingestion of clopidogrel (n=14) and compared to patients who did not receive clopidogrel (n=7).). FIG. 7B shows the difference in the phospho-Drp1-Ser616:total Drp1 ratio between control subjects and patients receiving clopidogrel. In this embodiment, a phospho-Drp1-Ser616:total Drp1 ratio of 1.25 as a cutoff to indicate activity, the patients receiving clopidogrel showed no activity, while controls uniformly showed activity. FIG. 7C shows an analysis of true positive and true negative rates.

FIG. 8A shows a Western blot indicating that stimulation of $P2Y_{12}$ is required for phosphorylation at Ser616. FIG. 8B is a Western blot showing that inhibitors of PI3 kinase, PKC, or Rho kinase do not block phosphorylation of Drp1 Ser-616 by SFLLRN (SEQ ID NO: 1).

FIG. 11A shows aggregometry tracings collected under standard conditions for 6 min. FIG. 11B shows the inhibition dose curve of cangrelor for platelet activation by ADP as plotted using the maximum percent aggregation observed for each concentration of cangrelor. 'NA Late' indicates a 'No Addition' sample analyzed simultaneous with the final dose of cangrelor (~3 hrs after draw) to ensure platelets were functioning normally at this time point. FIG. 11C shows a dose curve of cangrelor inhibition of platelet activation by ADP (20 µM) as analyzed using the Drp1 ratio assay with a chemiluminescence format.

FIG. 12A shows activation time in response to ADP (20 µM). FIG. 12B shows activation time in response to arachidonic acid (500 µg/mL). FIG. 12C shows activation time in response to SFLLRN (SEQ ID NO: 1) (25 µM).

DETAILED DESCRIPTION OF CERTAIN EMBODIMENTS OF THE INVENTION

Figure 1A:
FIGS. 1A-1C show Drp1 phosphorylation with different platelet agonists.

The disclosure relates, in some aspects, to methods, systems, and compositions for detecting the presence or absence of certain phosphorylated species of Drp1 protein (e.g., phospho-Drp-1-Ser616, phospho-Drp1-Ser637, etc.) in a subject, biological system, or biological sample. The disclosure is based, in part, on assays for detecting the absence of phospho-Drp1-Ser616 in a biological sample that has been stimulated with a platelet agonist. In some embodiments, the absence of phospho-Drp1-Ser616 in a sample comprising stimulated platelets is indicative of the responsiveness (e.g., sensitivity) to treatment with certain antiplatelet agents. In some embodiments, the presence of phospho-Drp1-Ser616 in a sample comprising stimulated platelets is indicative of the lack of responsiveness (e.g., resistance) to treatment with certain antiplatelet agents.

One advantage of methods described herein compared to currently available platelet functional assays is the ability of a single Drp1-Ser616 assay to detect the inhibition of platelets by multiple antiplatelet agents. As described further in the Examples section, assay methods described herein are, in some embodiments, able to detect a subject's sensitivity to certain antiplatelet agents, for example, clopidogrel, cangrelor, prasugrel, ticagrelor, ticlopidine, aspirin, cilostazol, dipyridamole, vorapaxar, forskolin, alprostadil, and terutroban. Thus, in some embodiments, methods described by the disclosure are useful as point-of-care (POC) assays to determine a subject's sensitivity to antiplatelet therapies and/or whether a subject has previously been exposed to one or more antiplatelet therapies.

Detection Methods

In some aspects, the disclosure relates to methods for detecting impaired platelet function in a biological sample. In some embodiments, the methods comprise detecting in a biological sample obtained from a subject the presence or absence of a Dynamin-related protein 1 (Drp1) that is phosphorylated at position Ser616 (phospho-Drp1-Ser616), wherein the biological sample has been stimulated with a platelet agonist and contacted with an agent that binds specifically to phospho-Drp1-Ser616, wherein the absence of phospho-Drp1-Ser616 in the sample following stimulation indicates impaired platelet function in the subject. The skilled artisan also recognizes that, in some embodiments, methods of the disclosure comprise detecting the presence or absence of phospho-Drp1-Ser617, wherein the presence of phospho-Drp1-Ser637 in the sample following stimulation indicates impaired platelet function in the subject.

A biological sample can be obtained from any suitable subject, for example a mammalian subject, such as a human, mouse, rat, dog, cat, pig, hamster, etc. In some embodiments, a biological sample is obtained from a human subject. In some embodiments, a biological sample is subjected to a preparative method, for example cell lysis, platelet isolation and/or purification, etc. In some embodiments, a biological sample is stimulated with a platelet agonist (e.g., stimulated with a platelet agonist prior to being contacted with an agent that binds specifically to phospho-Drp1-Ser616).

The disclosure is based, in part, on methods for detecting impaired platelet function in a subject or a biological sample obtained from a subject. Thus, in some embodiments, a biological sample comprises a population (e.g., one or more platelets). A biological sample comprising platelets may or may not contain other biological components (red blood cells, white blood cells, plasma, etc.) and may or may not be processed after being obtained from a subject. Methods of obtaining biological samples from a subject are generally known and are described, for example, by Levine et al. (1981) *Thrombosis Research* 24(5-6):1-15. In some embodiments, the biological sample is whole blood. In some embodiments, the biological sample is platelet rich plasma or purified platelets.

The disclosure is based, in part, on assays for detecting the presence or absence of phospho-Drp1-Ser616 in a sample comprising stimulated platelets. Generally, stimulated platelets refers to platelets that have been activated. Activated platelets typically are characterized by one or more of the following: exocytosis of the dense granules and alpha granules, activation of the membrane enzyme phospholipase A2 leading to the formation of thromboxane A2 (TXA2), platelet aggregation, etc. In some embodiments, platelets are stimulated (e.g., activated) in response to exposure to a platelet agonist.

Platelet agonists are agents that bind to a platelet receptor or increase the activity of a platelet protein and result in activation of the platelet. Platelet receptors include, but are not limited to, G-protein-coupled receptors, integrins, leucine-rich repeat receptors, selectins, tetranspanins, transmembrane receptors (e.g., ADP receptors, PAR receptors, etc.), prostaglandin receptors, lipid receptors, immunoglobulin family receptors, and tyrosine kinase receptors. Additional platelet receptors are described, for example by Saboor et al. (2013) *Pak J Med Sci.* 29(3): 891-896. In some embodiments, a platelet agonist binds to a transmembrane platelet receptor. In some embodiments, the transmembrane receptor is a protease-activated-receptor 1 (PAR1) receptor (also referred to as a thrombin receptor). Examples of PAR1 receptor agonists include, but are not limited, to serine proteases (e.g., thrombin, plasmin, trypsin, etc.), SFLLRN (SEQ ID NO: 1) peptide, AY-NH$_2$, 2-furoyl-LIGRLO-amide (SEQ ID NO: 3), LRGILS-NH$_2$ (SEQ ID NO: 4), TFLLR-NH$_2$ (SEQ ID NO: 5), TRAP-6, etc. In some embodiments, binding of an agonist to a platelet receptor results in activation of the platelet (e.g., activation of the platelet receptor).

In some embodiments, a platelet agonist binds to or increases the activity of a platelet protein (e.g. a protein involved in the platelet activation pathway that is not a platelet receptor protein). In some embodiments, a platelet protein is a cyclooxygenase (COX) protein. COX proteins (also referred to as prostaglandin-endoperoxide synthase (PTGS) proteins) catalyze synthesis of thromboxane and prostaglandins from arachidonic acid. In some embodiments, a COX protein is COX-1 or COX-2. In some embodiments, a platelet agonist is arachidonic acid.

A platelet (e.g., a platelet receptor, a platelet protein, etc.) is generally stimulated with an effective amount of a platelet agent (e.g., a platelet agonist). In some embodiments, an effective amount of a platelet agonist is the amount of a platelet agent that, when administered to the platelet, results in activation (e.g., triggering of activation molecules such as thromboxane A2, ADP, thrombin, platelet activating factor (PAF), exocytosis of dense granules and alpha granules, etc.).

The timing of administration of platelet stimulation (e.g., stimulating the platelets of a biological sample or subject) can vary. In some embodiments, a platelet is stimulated (e.g., administered or contacted) with a platelet agent between about 1 minute and about 24 hours prior to detecting the presence or absence of phospho-Drp1-Ser616 or phospho-Drp1-Ser37. In some embodiments, a platelet is stimulated with a platelet agent between about 1 minute and 60 minutes, about 10 minutes and 120 minutes, about 30 minutes and 3 hours, about 1 hour and about 5 hours, or about 3 hours and about 24 hours prior to detecting the presence or absence of phospho-Drp1-Ser616 or phospho-Drp1-Ser37. In some embodiments, platelets are stimulated with a platelet agonist between about 1 minute and 13 minutes prior to detecting the presence or absence of phospho-Drp1-Ser616 or phospho-Drp1-Ser37. In some embodiments, a platelet is stimulated with a platelet agonist, lysed and tested between about 5 minutes and 240 minutes prior to detecting the presence or absence of phospho-Drp1-Ser616 or phospho-Drp1-Ser37.

The disclosure is based, in part, on agents that bind specifically to certain phosphorylated forms of Drp1 proteins, for example, phospho-Drp1-Ser616 or phospho-Drp1-Ser37. The term "binds specifically" generally refers to preferential binding of a target molecule (such as a protein, for example, phospho-Drp1-Ser616) by a binding agent (e.g., an antibody (e.g., monoclonal antibody, polyclonal antibody, etc.) or fragment thereof, peptide, small molecule, aptamer, etc.). A binding agent "specifically binds" to a target if it binds with greater affinity, avidity, more readily, and/or with greater duration than it binds to other substances. In some embodiments, an agent that specifically binds to a Drp1 protein (e.g., phospho-Drp1-Ser616) may bind to that protein with at least 10%, at least 20%, at least 30%, at least 40%, at least 50%, at least 60%, at least 70%, at least 80%, at least 90%, or more, greater affinity as compared to binding to other substances. In some embodiments, an agent that specifically binds to a phosphorylated Drp1 protein (e.g., phospho-Drp1-Ser616) may bind to that protein with at least 10%, at least 20%, at least 30%, at least 40%, at least 50%, at least 60%, at least 70%, at least 80%, at least 90%, or more, greater affinity as compared to binding to a non-phosphorylated Drp1 protein. In some embodiments, an agent that specifically binds to a Drp1 protein (e.g., phospho-Drp1-Ser616) may bind to that protein with at least 2-fold, at least 5-fold, at least 10-fold, at least 50-fold, at least 100-fold, at least 500-fold, or more, of the affinity for binding to that protein as compared to its binding to other substances.

Generally, an agent may be an antibody (e.g., monoclonal antibody, polyclonal antibody, etc.) or fragment thereof, peptide, small molecule, or an aptamer. In some embodiments, an agent is an antibody or fragment thereof that binds specifically to phospho-Drp1-Ser616. In some embodiments, an agent is an antibody or fragment thereof that binds specifically to phospho-Drp1-Ser637. In some embodiments, an agent (e.g. antibody) that binds specifically to phospho-Drp1-Ser616 does not bind to phospho-Drp1-Ser637. In some embodiments, an agent (e.g. antibody) that binds specifically to phospho-Drp1-Ser637 does not bind to phospho-Drp1-Ser616. Examples of antibodies that bind specifically to Drp1 protein that is phosphorylated at position Ser616 or Ser637 are described, for example, in Koseoglu et al. (2013) *Arterioscler Thromb Vasc Biol.* 33(3):481-8.

The presence or absence of phospho-Drp1-Ser616 and/or phopho-Drp1-Ser637 can be detected by any suitable method. In some embodiments, the presence or absence of a phosphorylated Drp1 protein is detected by a binding assay, for example, ELISA. In some embodiments, the method of detecting comprises contacting the sample with an agent (e.g., an antibody, such as an antibody labeled with a detectable label) that binds specifically to phospho-Drp1-Ser616. In some embodiments, the method of detecting comprises contacting the biological sample with an agent (e.g., an antibody) that binds specifically to phospho-Drp1-Ser616 to form a complex, and then contacting the complex with a detectable secondary reagent that binds specifically to the portion of the complex comprising the agent. A detectable secondary reagent may be an antibody (e.g., a monoclonal antibody, polyclonal antibody, etc.) or a fragment thereof, antibody fragment, peptide, aptamer, nucleic acid, or small molecule. In some embodiments, a detectable secondary reagent comprises a detectable label. In some embodiments, the detectable secondary reagent comprises a fluorescent tag or an epitope tag (e.g., a FLAG tag, HIS-tag, etc.).

In some embodiments, the presence or absence of a phosphorylated Drp1 protein is detected by chemiluminescence assay (e.g., a chemiluminescence assay comprising a stable peroxide solution and a luminol reagent), an electrochemiluminescence immunoassay, automated immunoanalyzer assay, or electrical impedance spectroscopy. Methods of detecting protein binding are described, for example in *The Immunoassay Handbook: Theory and Applications of Ligand Binding, ELISA and Related Techniques* (2013) Wild, ed.; Elsevier (Oxford, UK). In some embodiments, a phosphorylated Drp1 protein (e.g., phospho-Drp1-Ser616 or phospho-Drp1-Ser37) is detected between about 5 minutes and 240 minutes after stimulation with a platelet agonist. In some embodiments, a phosphorylated Drp1 protein (e.g., phospho-Drp1-Ser616 or phospho-Drp1-Ser37) is detected more than 240 minutes after stimulation with a platelet agonist.

In some embodiments, the disclosure relates to detecting the presence or absence of certain phosphorylated forms of Drp1 (e.g., phospho-Drp1-Ser616, phospho-Drp1-Ser637). The skilled artisan recognizes that the presence or absence of phosphorylated forms of Drp1 may also be expressed as a ratio of phospho-Drp1-Ser616 detected in a sample to total Drp1 detected in a sample. The ratio of Ser616: total Drp1 in a biological sample may range from about 100:1 to about 1:100 (e.g., 100:1, 50:1, 25:1, 10:1, 5:1, 2:1, 1:1, 1:2, 1:5, 1:10, 1:25, 1:50, 1:100, or any range between). Accordingly, in some embodiments, phospho-Drp1-Ser616 is "absent" in a sample when a sample comprises a lower ratio of phospho-Drp1-Ser616: total Drp1 (e.g. a ratio below 1.25). In some embodiments, phospho-Drp1-Ser616 is "present" in a sample when a sample comprises a higher ratio of phospho-Drp1-Ser616: total Drp1 (e.g., a ratio above 1.25).

In some embodiments, the presence or absence of phospho-Drp1-Ser616 or phospho-Drp1-Ser637 is detected relative to a control sample. A "control sample" refers to a biological sample that is obtained from a subject that does not have impaired platelet function, for example, a subject that has not been exposed to an antiplatelet agent. In some embodiments, a control sample is obtained from a subject that does not have a cardiovascular disease or disorder, or a cerebrovascular disease or disorder. In some embodiments, a "normal" or "baseline" amount (e.g., a threshold amount) of phospho-Drp1-Ser616 and/or total Drp1 is detected in a control sample. In some embodiments, a "normal" or "baseline" ratio of phospho-Drp1-Ser616:total Drp1 is detected in a control sample. In some embodiments, the presence of phospho-Drp1-Ser616 in a biological sample is an amount that is above a threshold amount or threshold ratio in a control sample. In some embodiments, reduced phospho-Drp1-Ser616 (or the absence of phospho-Drp1-Ser616) in a biological sample is an amount that is below a threshold amount or threshold ratio in a control sample. In some embodiments, a threshold ratio of phospho-Drp1-Ser616: total Drp1 ranges from about 0.5 to about 2.0 (e.g., about 0.5, 0.6, 0.7, 0.8, 0.9, 1.0, 1.1, 1.2, 1.3, 1.4, 1.5, 1.6, 1.7, 1.8, 1.9, or 2.0). In some embodiments, a threshold ratio of phospho-Drp1-Ser616: total Drp1 is greater than 2.0. In some embodiments, a threshold ratio of phospho-Drp1-Ser616: total Drp1 is 1.25.

In some aspects, methods described by the disclosure detect the absence of phospho-Drp1-Ser616 in the sample following platelet stimulation, which is indicative of impaired platelet function in the subject. In some embodiments, impaired platelet function in a subject results from exposure of the subject to an antiplatelet agent (e.g., a platelet antagonist). The disclosure is based, in part, on the unexpected discovery that phosphorylation of Ser616 on Drp1 requires the release of ADP and subsequent stimulation of the $P2Y_{12}$ receptor. Thus, in some embodiments, absence of phospho-Drp1-Ser616 in a sample indicates that the subject from which the sample has been obtained has been previously exposed to a platelet antagonist which binds to a transmembrane receptor, for example, an Adenosine Diphosphate (ADP) receptor. In some embodiments, the ADP receptor is a $P2Y_{12}$ receptor or a thromboxane (TP) receptor. In some embodiments, a transmembrane receptor is a PAR1 receptor. Examples of antiplatelet agents that bind to transmembrane receptors include, but are not limited to, clopidogrel, cangrelor, prasugrel, ticagrelor, ticlopidine, vorapaxar, and terutroban.

In some embodiments, the disclosure is based on detection of the absence of phospho-Drp1-Ser616 in a sample indicating that the subject from which the sample has been obtained has been previously exposed to a platelet antagonist which inhibits a platelet protein, for example, a COX protein. In some embodiments, absence of phospho-Drp1-Ser616 indicates that a subject has previously been exposed to a COX-protein inhibitor, for example, aspirin or a non-steroidal anti-inflammatory drug (NSAID). Examples of NSAIDs include celecoxib (Celebrex), diclofenac (Cambia, Cataflam, Voltaren-XR, Zipsor, Zorvolex), diflunisal, etodolac, ibuprofen (Motrin, Advil), indomethacin (Indocin), ketoprofen, ketorolac, nabumetone, naproxen (Aleve, Anaprox, Naprelan, Naprosyn), oxaprozin (Daypro), piroxicam (Feldene), salsalate, sulindac, and tolmetin.

In some embodiments, the disclosure is based on detection of absence of phospho-Drp1-Ser616 in a sample indicating that the subject from which the sample has been obtained has been previously exposed to a platelet antagonist which inhibits a platelet protein, for example, a phosphodiesterase protein. In some embodiments, the phosphodiesterase protein is phosphodiesterase 3A (PDE3A). In some embodiments, absence of phospho-Drp1-Ser616 indicates that a subject has previously been exposed to a PDE3A inhibitor, for example cilostazol, dipyridamole, cilostamide, ibudilast, milrinone, or amrinone.

The time from which a subject has previously been exposed to an antiplatelet agent (e.g., a platelet antagonist) can vary. In some embodiments, a subject has been exposed to (e.g., administered) an antiplatelet agent between about 1 minute and about 30 days prior to a biological sample being obtained from the subject. In some embodiments, a subject has been exposed to (e.g., administered) an antiplatelet agent between about 1 minute and 60 minutes, about 5 minutes and 5 hours, about 30 minutes and 24 hours, about 1 day and 10 days, or about 7 days and 30 days prior to a biological sample being obtained from the subject.

Therapeutic Indications

In some aspects, methods described by the disclosure are useful for determining the sensitivity of the subject to certain antiplatelet therapies. The disclosure is based, in part, on the discovery that detecting the absence of phospho-Drp1-Ser616 protein in stimulated platelets is indicative of platelet responsiveness to an antiplatelet agent, whereas the presence of phospho-Drp1-Ser616 protein is indicative of lack of platelet responsiveness to the antiplatelet agent. For example, if a biological sample (e.g., a sample comprising platelets) obtained from a subject previously treated with cangrelor (a $P2Y_{12}$ platelet receptor antagonist) is stimulated with a platelet agonist (e.g., SFLLRN (SEQ ID NO: 1) peptide) and the presence of phospho-Drp1-Ser616 is detected, the subject is resistant to treatment with platelet antagonists that function via the $P2Y_{12}$ platelet receptor. In some embodiments, the subject is administered an antiplatelet agent that is not a P2Y$_{12}$ platelet receptor antagonist (e.g., aspirin, a COX-2 inhibitor, etc.) based upon detecting the presence of phospho-Drp1-Ser616 in the sample.

In some aspects, methods of determining sensitivity to certain classes of antiplatelet therapies are useful for treating a subject having or suspected of having a cardiovascular disease or a cerebrovascular disease.

In some embodiments, if a subject is determined to lack sensitivity (e.g., to be resistant) to a class of antiplatelet agents using a method described herein, that subject is administered an antiplatelet agent from a class that is different from the class to which the subject lacks sensitivity. For example, if a subject is determined to be resistant to COX-2 inhibitors using a method as described herein, that subject may be administered a P2Y$_{12}$ platelet receptor antagonist (e.g., cangrelor) instead.

Alternatively, in some embodiments, a subject that is determined to lack sensitivity (e.g., to be resistant) to a class of antiplatelet agents using a method described herein may be administered an increased dose of the same antiplatelet agent. In some embodiments, a subject is administered an increased (e.g., a doubling dose) of the same antiplatelet therapy. As used herein, a "doubling dose" refers to a dose of an antiplatelet agent that is 2-fold the amount (e.g., measured by weight or volume of active ingredient) higher than the dose of antiplatelet agent that the subject currently is administered.

In some embodiments, a subject is administered a dose that is about 10% higher, 20% higher, 30% higher, 40% higher, 50% higher, 60% higher, 70% higher, 80% higher, 90% higher, 100% higher, 150% higher, 200% higher, or more, relative to the dose of antiplatelet agent that the subject is currently receiving.

In some embodiments, methods described by the disclosure are useful for determining whether a subject who has been exposed to certain antiplatelet therapies is an acceptable candidate for an invasive procedure (e.g., surgery). Accordingly, in some aspects, the disclosure relates to a method for determining the presence or absence of phospho-Drp1-Ser616 in a biological sample obtained from a subject, and delaying performance of an invasive procedure on the subject if the absence of phospho-Drp1-Ser616 is detected in the sample.

In some embodiments, an invasive procedure is delayed by between 6 hours and 6 weeks based upon detecting a phospho-Drp1-Ser616:total Drp1 ratio in an amount of less than a threshold ratio (e.g., a phospho-Drp1-Ser616:total Drp1 ratio of 1.25). In some embodiments, an invasive procedure is delayed for 1 day, 2 days, 5 days, 7 days, 10 days, 14 days, 30 days, 180 days, or 365 days based upon detecting a phospho-Drp1-Ser616:total Drp1 ratio in an amount of less than a threshold ratio (e.g., a phospho-Drp1-Ser616:total Drp1 ratio of 1.25) in the sample.

EXAMPLES

Example 1: Materials and Methods

MAP Kinase Inhibition Studies

Using twice washed platelets, 400 µL aliquots were incubated at 37° C. for 30 min with SB203580 (20 µM), PD0325901 (5 µM), SP600125 (5 µM) or left untreated and then activated with respective agonist for 10 min at 37° C. Subsequently, 100 µL of 5×RIPA buffer was added and samples were lysed on ice for minimum of 15 min. Samples were stored at −80° C. until assayed by ELISA.

Dose Response Curves with Vorapaxar and Cangrelor

Serial dilutions of Vorapaxar and Cangrelor were prepared in DMSO. To 400 µL aliquots of washed platelets (WP), 4 µL of platelet inhibitor/DMSO dilutions was added and incubated at 37° C. for 30 min before being activated with SFLLRN (SEQ ID NO: 1) (10 µM) for 10 min at 37° C. Vehicle only samples were also prepared and incubated at 37° C. Samples were subsequently lysed with 5×RIPA buffer and stored at −80° C. until assayed by ELISA.

Dose Response Curve with Aspirin

Dilutions of Tyrode's buffer+3 mM aspirin were prepared. A modified platelet wash protocol was then performed. PRP [supplemented with 20% ACD (v/v) and PGE1 (1 µM)] was spun at 800 g for 12 min. After removal of the supernatant, platelet pellet was resuspended in Tyrode's buffer and allowed to rest at 37° C. for minimum of 25 min. Platelets were counted by Hemavet and were again supplemented with ACD and PGE1 before being aliquoted into microcentrifuge tubes and spun at 800 g for 12 min. Aliquots were of sufficient volume to permit a final platelet count of approximately 4×10$^5$/µL when platelet pellet was resuspended in 400 µL of Tyrode's buffer or Tyrode's buffer/aspirin dilution. After resuspension, samples were incubated at 37° C. for 1 hr before being activated for 10 min at 37° C. with arachidonic acid (Bio Data Corp. Horsham, PA) at a final concentration of 10 µg/mL. Samples were lysed with 100 µL 5×RIPA buffer on ice for a minimum of 15 min before being stored at −80° C. until assayed by ELISA.

Assay of Clopidogrel Patient Samples

Platelet-rich plasma (PRP) samples from patients on Clopidogrel were obtained. PRP was also obtained from healthy donors not receiving antiplatelet therapy to provide control samples. PRP was washed using previously published protocols. Platelet count was ultimately measured and diluted with HTG buffer as necessary to obtain a count between 2×105—4×105/µL. Three aliquots of 400 µL from both patient and control donors were dosed with SFLLRN (SEQ ID NO: 1) (10 µM), thrombin (1 U/mL), or remained untreated (resting sample). After 10 min at 37° C., 100 µL of 5×RIPA buffer with phosphatase and protease inhibitor was added to each sample and lysed on ice for a minimum of 15 min prior to being stored at −80° C. until assayed by ELISA.

ELISA Protocol

Capture antibody (Ms Drp1 mAb) diluted in Tris-buffered saline (TBS) was incubated on plates at RT (2 hrs) or at 4° C. overnight. Wells were washed three times with TBS+ 0.1% Tween 20 (TBST). Wells were blocked with 3% BSA in TBST for a minimum of 1.5 hrs. After triple washing with TBST, diluted platelet lysate samples were incubated at RT for 2 hrs or at 4° C. overnight. Wells were again washed with TBST and incubated with either Rb Drp1 or p-Drp1 (Ser616) mAb at RT for 1 hr. After washing, wells were incubated with secondary antibody conjugated to HRP (anti-Rb) at RT for 1 hr. Wells were washed a final time and before TMB reagent was added and allowed to develop. The reaction was halted with the addition of 1 M HCl. Absorbances were subsequently measured at 450 nm on SpectraMax microplate reader (Molecular Devices, LLC. Sunnyvale, CA).

Example 2: Drp1 Phosphorylation Assays

Figure 1B:
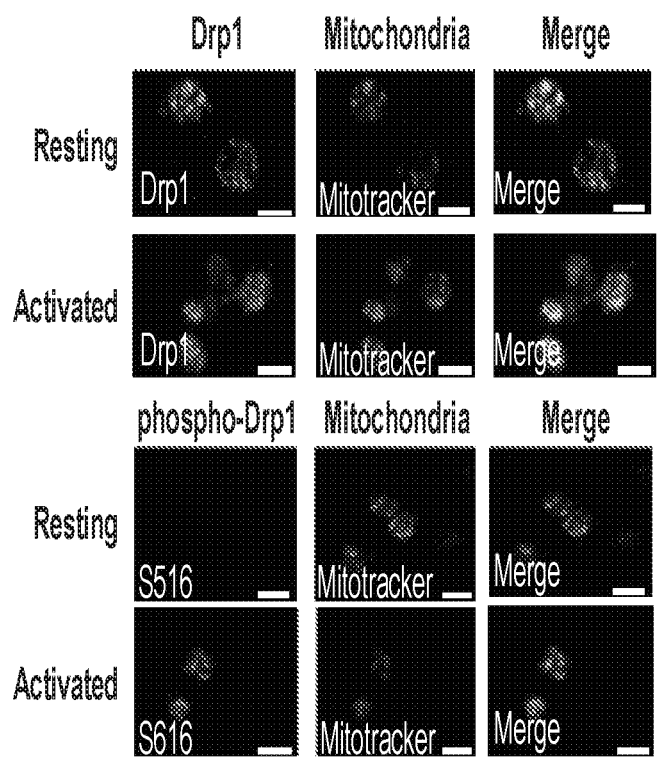
Figure 1C:
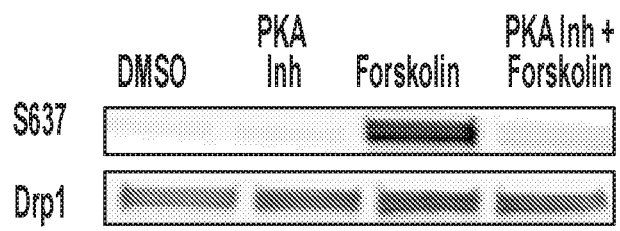

Studies to evaluate signaling pathways involved in phosphorylation of Drp1 agonist sensitivity were performed. Phosphorylation of Drp1 at S616 was observed following incubation with agonists that stimulate activating G protein-coupled receptors (SFLLRN (SEQ ID NO: 1), U46619, etc.) or the tyrosine kinase-linked receptor GPVI (collagen) (FIG. 1A). Drp1-Ser616 co-localized with mitochondria following platelet activation with strong agonists (FIG. 1B). None of the agonists tested elicited Drp1-S637 phosphorylation. In contrast, activation of adenylyl cyclase (forskolin) resulted in Drp1-5637 phosphorylation, but failed to activate 5616-Drp1 (FIG. 1C). These results indicate reagents that activate platelets elicit Drp1-Ser616 phosphorylation, while reagents that pacify platelets through elevation of cAMP stimulate Drp1-Ser637 phosphorylation.

In nucleated cells, cAMP-dependent kinase (PKA) has been observed to directly phosphorylate Drp1 at S637. To assess the mechanism by which elevation of cAMP results in Drp1-Ser637 phosphorylation in platelets, the effects of the PKA inhibitor, KT5720, on Drp1-Ser637 phosphorylation were evaluated. Incubation with KT5720 completely abolished forskolin-mediated Drp1-Ser637 phosphorylation (FIG. 1C), confirming involvement of PKA. These studies demonstrate two discrete, pathways for phosphorylating Drp1, each of which acts at a different site on the substrate.

Figure 2A:
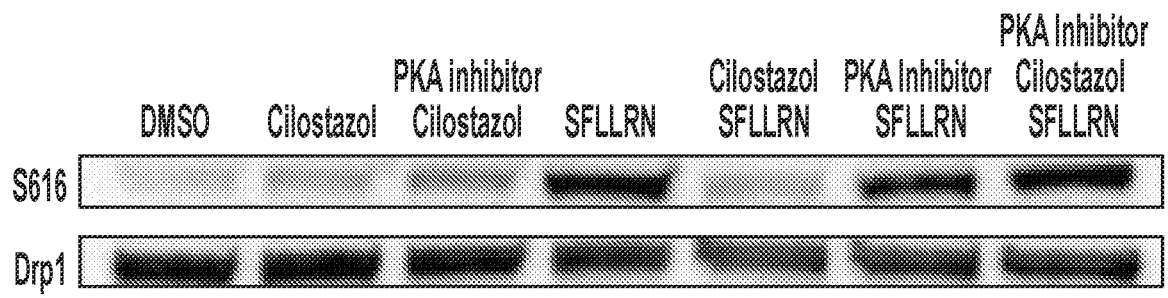
FIGS. 2A-2C show phosphorylation of Drp1 Ser616.
Figure 2B:
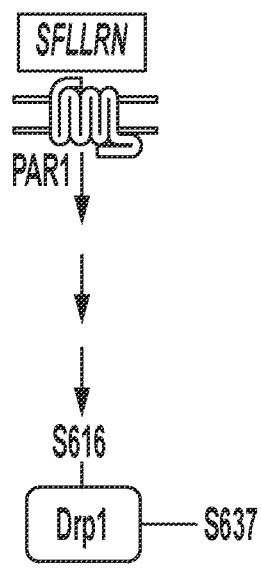
Figure 2C:
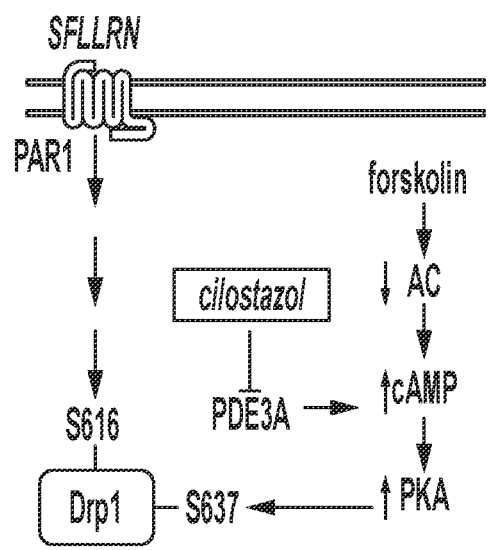

The observation that phosphorylation of Drp1 at Ser616 and Ser637 did not occur at the same time indicated that phosphorylation of Ser637 prevents phosphorylation at Ser616. To evaluate the mutually exclusive phosphorylation of Ser616 and Ser637, the effects of incubating platelets with cilostazol, which inhibits phosphodiesterase 3A, elevating cAMP levels and activating PKA, were investigated. It was observed that cilostazol treatment blocks SFLLRN (SEQ ID NO: 1)-induced phosphorylation of Ser616 (FIG. 2A). Addition of a PKA inhibitor reversed the inhibitory effect of cilostazol on SFLLRN (SEQ ID NO: 1)-induced phosphorylation of Ser616. These data indicate that while stimulation by strong agonists results in Drp1-Ser616 phosphorylation (FIG. 2B), phosphorylation at Drp1-Ser637 precludes Drp-Ser616 phosphorylation (FIG. 2C).

Figure 3A:
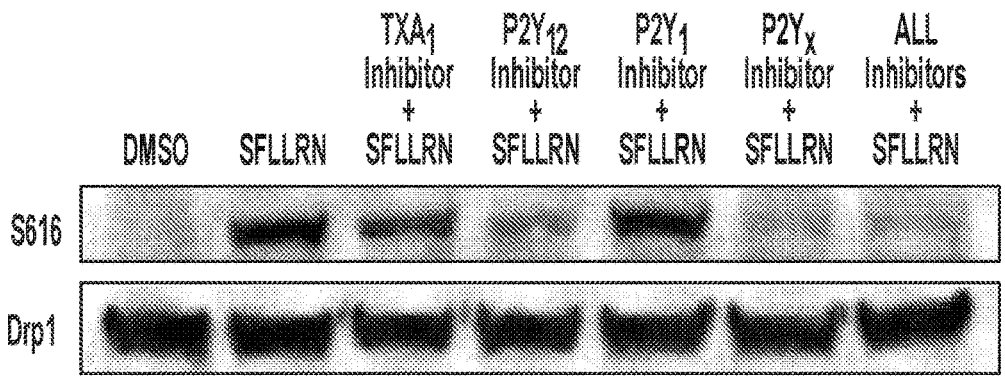
FIGS. 3A-3C show representative data for Drp1 phosphorylation.
Figure 3B:
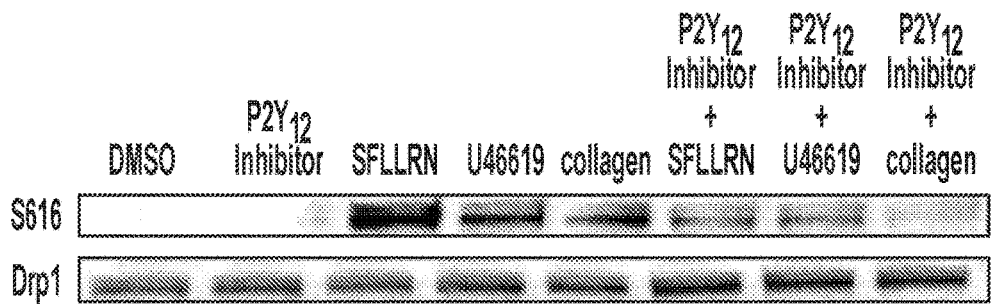
Figure 3C:
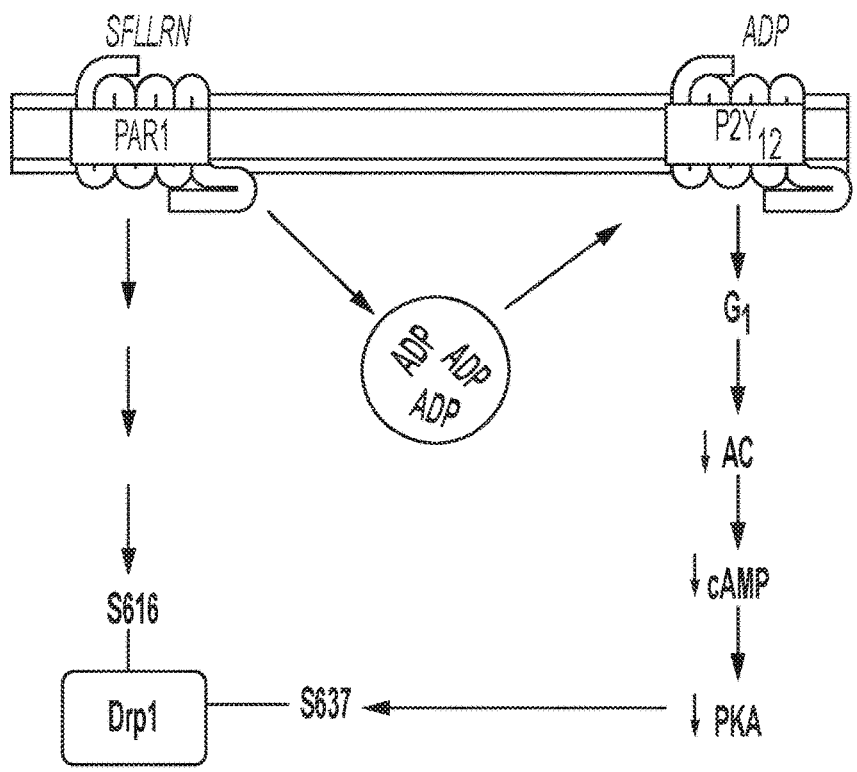
Figure 8A:
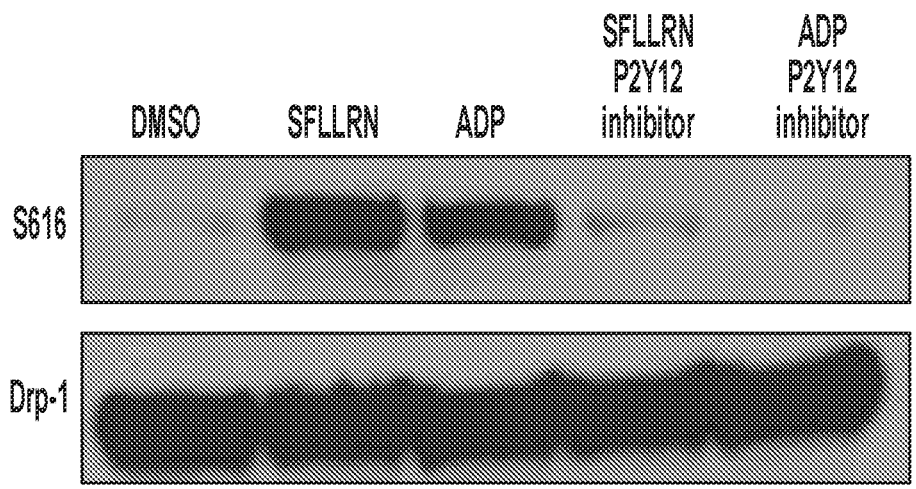
FIGS. 8A-8B show Western blot data for $P2Y_{12}$-mediated phosphorylation of Drp1 Ser616.

Given that the two signaling pathways for Drp1 phosphorylation are mutually exclusive, the question of whether the activating pathway prevents phosphorylation of Drp1-Ser637 so as to enable phosphorylation of Drp1-Ser616 was investigated. Activation with strong agonists releases several autocrine factors from platelets. To determine whether autocrine stimulation following incubation with strong agonists serves a role in Drp1-Ser616 phosphorylation, the effects of inhibition of P2Y$_{12}$ (using MRS 2395), P2Y$_1$ (using A3P5P), and thromboxane generation (using aspirin) were assessed. Only combinations that included inhibition of P2Y$_{12}$ blocked SFLLRN (SEQ ID NO: 1)-induced Drp1-Ser616 phosphorylation (FIG. 3A). Incubation of platelets with ADP resulted in 5616-Drp1 phosphorylation, which was inhibited by MRS 2395 (FIG. 8A). Further, inhibition of P2Y$_{12}$ blocked Drp1-Ser616 phosphorylation induced by SFLLRN (SEQ ID NO: 1), U46619, or collagen (FIG. 3B) These results indicate that platelet activation results in the release of ADP from storage granules activating P2Y$_{12}$, which is a Gai-linked receptor that inhibits adenylyl cyclase activity and prevents activation-induced increases in cAMP and PKA activity (FIG. 3C).

Figure 8B:
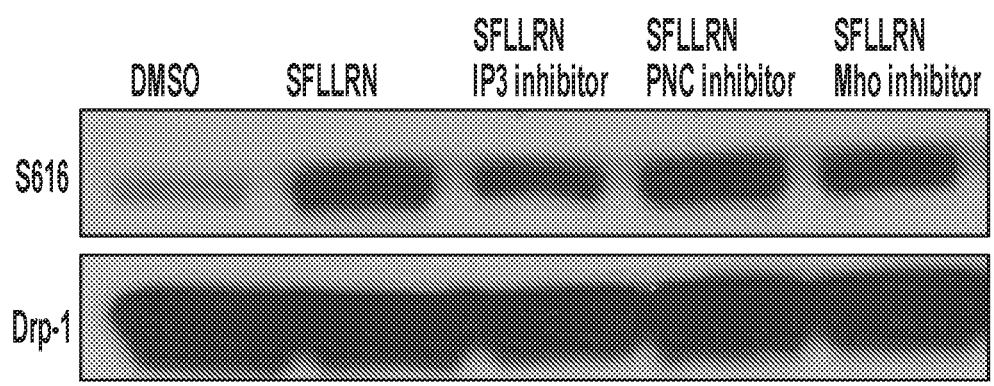

The effects of wortmannin on phosphorylation of Drp1 at Ser616 was investigated. Wortmannin does not affect Ser616 phosphorylation of Drp1 (FIG. 8A). Similarly, inhibitors of protein kinase C and Ro 31-8220 failed to inhibit PAR1-mediated Drp1-Ser616 phosphorylation (FIG. 8B).

Figure 4A:
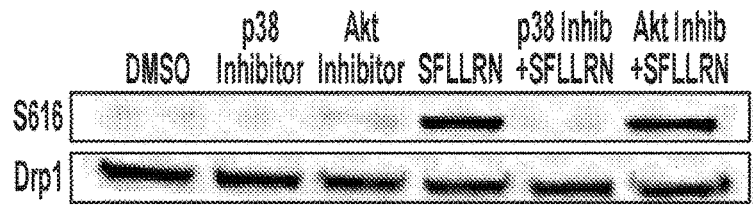
FIGS. 4A-4G show representative data for Drp1 phosphorylation.
Figure 4B:
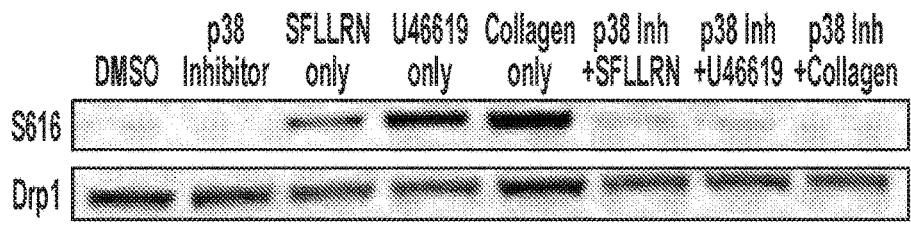
Figure 4C:
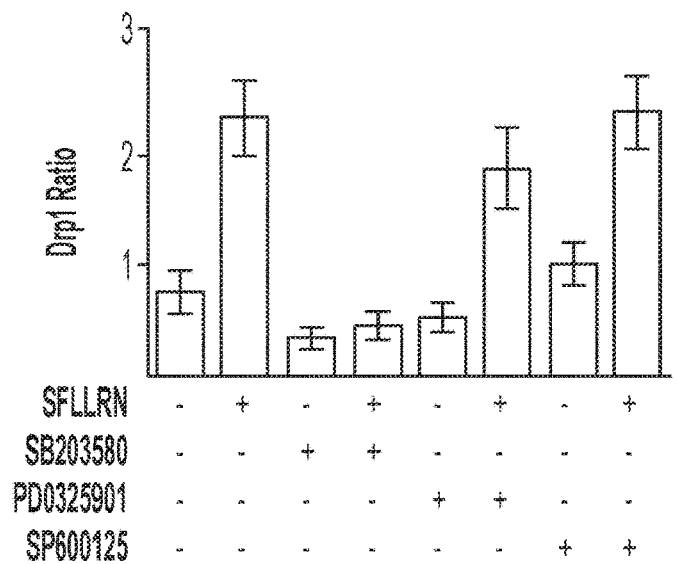
Figure 4D:
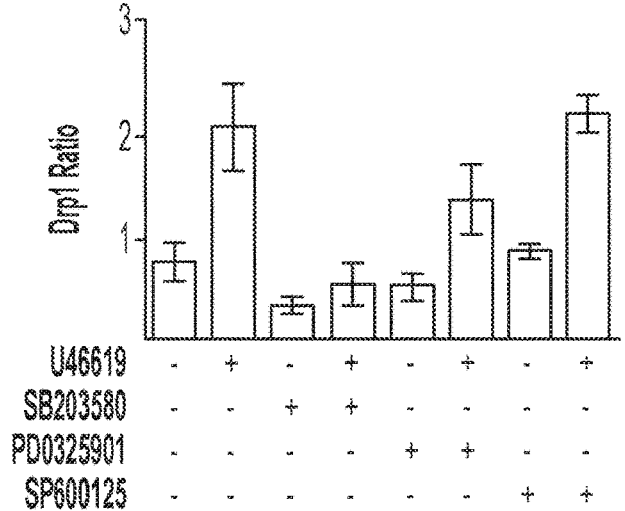
Figure 4E:
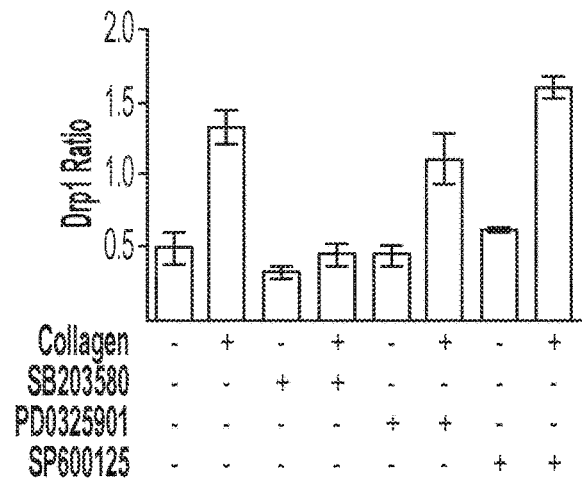
Figure 4F:
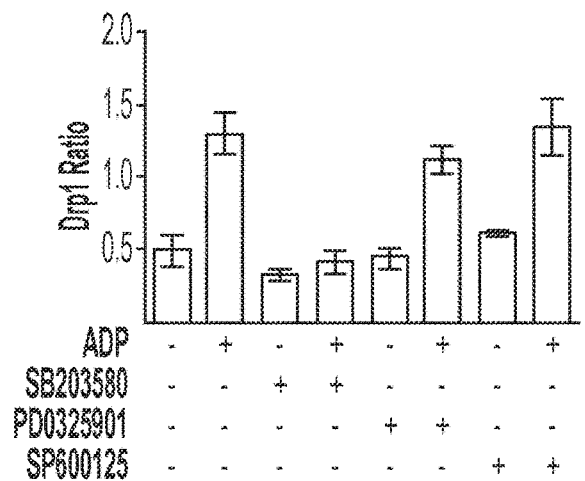
Figure 4G:
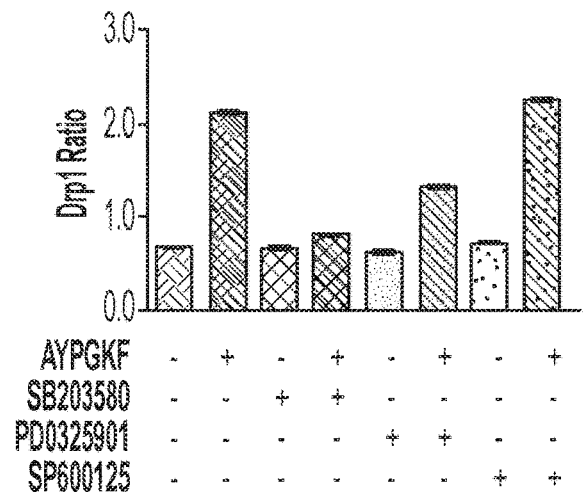

In platelets, it was observed that SFLLRN (SEQ ID NO: 1)-induced Drp1-Ser616 phosphorylation was inhibited by a p38-selective antagonist (SB203580), but not by an Akt antagonist (FIG. 4A). Inhibition of p38 blocked Drp1-Ser616 phosphorylation by several agonists (FIG. 4B). Several MAPK pathways are active in platelets. To assess which MAPKs function in Drp1-Ser616, platelets were incubated with SB203580, a MEK1/2 antagonist (PD0325901), or a JNK inhibitor (SP600125) and evaluated agonist-induced Drp1-Ser616 phosphorylation. Inhibition of p38 potently blocked phosphorylation of Drp1-Ser616 induced by the PAR1 agonist SFLLRN (SEQ ID NO: 1), the TP receptor agonist U46619, collagen, ADP, or the PAR4 agonist AYPGKF (SEQ ID NO: 2) (FIGS. 4A-4G). Inhibition of MEK1/2, which signals directly to ERK1/2, demonstrated modest inhibition of Drp1-Ser616 phosphorylation, regardless of agonist. Inhibition of JNK failed to inhibit agonist-induced stimulation of Drp1-Ser616 (FIGS. 4A-4G). Taken together, these data indicate that phosphorylation of Drp1-Ser616 requires simultaneous inhibition of PKA signaling and phosphorylation by MAPKs, primarily p38.

Mapping of platelet signaling pathways can inform the development of assays to evaluate sensitivity to antiplatelet agents. Signaling to adenylyl cyclase to increase VASP phosphorylation, for example, has been used to assess clopidogrel resistance. The basis for this assay is to determine the effect of P2Y$_{12}$-mediated signaling on Gai activation of adenylyl cyclase using VASP phosphorylation as a readout, since VASP is phosphorylated by PKA. The VASP assay typically requires an initial incubation of platelets with PGE1 to activate Gai through EP3 receptors. In the presence of ADP, this baseline VASP phosphorylation is inhibited. However, if P2Y$_{12}$ is blocked by clopidogrel, then ADP will not affect PGE1-mediated VASP phosphorylation.

Whether Drp1-Ser616 could be used as a more direct readout of P2Y$_{12}$ function was investigated. While the VASP phosphorylation assay has been used clinically to detect clopidogrel resistance, it is a flow cytometry-based assay that requires several steps and is not easily performed in a point of care format and requires substantial technician time in a central lab. The dual control of Drp1 phosphorylation that is based upon endogenous ADP release from dense granules, in some embodiments, provides a more convenient assay for evaluating P2Y$_{12}$ inhibition, since it does not call for PGE1 exposure prior to ADP stimulation. In addition, a Drp1-Ser616 phosphorylation-based assay is useful, in some embodiments, for evaluating platelet antagonists that act through different mechanisms.

Figure 5A:
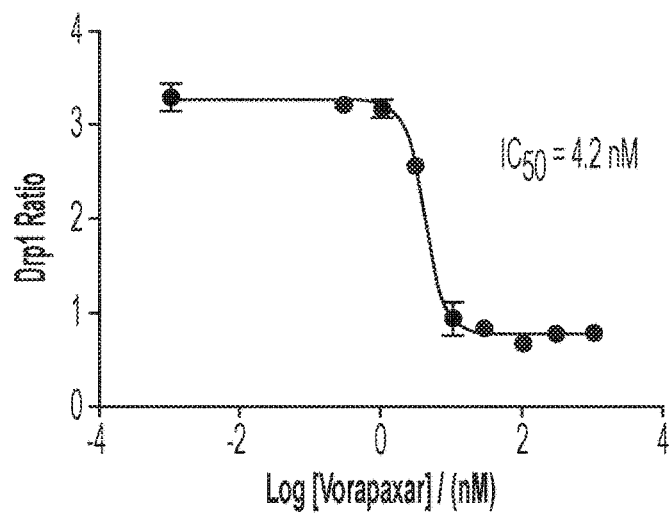
FIGS. 5A-5C show dose response curves of antiplatelet agents with respect to Drp1 phosphorylation ratio (phospho-Drp1-Ser616/total Drp1).
Figure 5B:
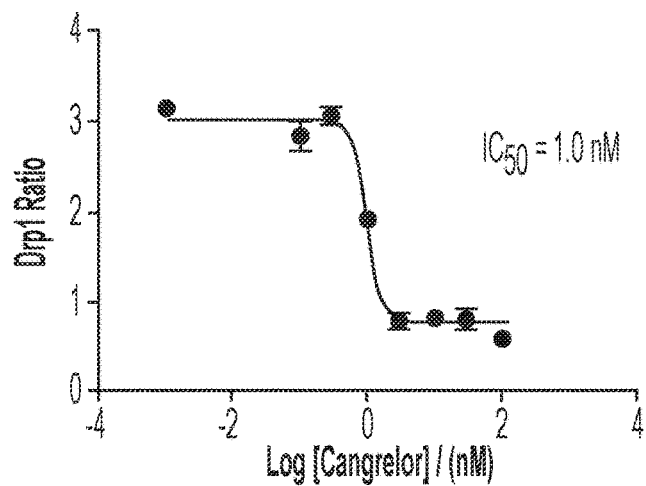
Figure 5C:
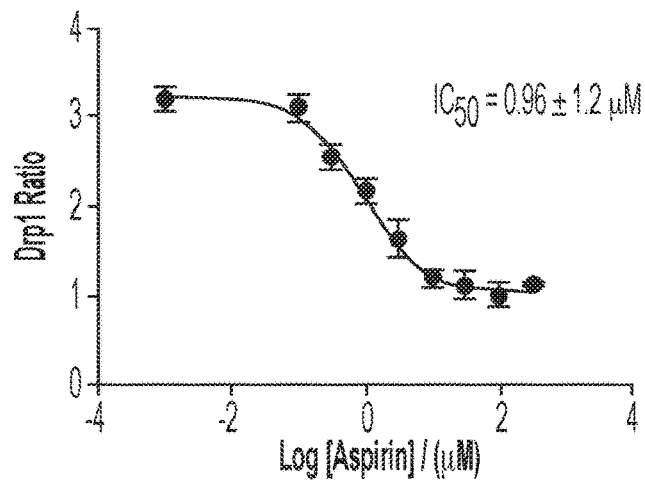

Platelets were stimulated with the PAR1 agonist SFLLRN (SEQ ID NO: 1), which is a strong secretagogue for dense granules. This assay was very sensitive to the FDA-approved PAR1 inhibitor, vorapaxar, with an IC50 of approximately 5 nM (FIG. 5A). To determine whether Drp1-Ser616 phosphorylation could be used to detect P2Y$_{12}$ inhibition, the effects of the FDA-approved P2Y$_{12}$ inhibitor cangelor on SFLLRN (SEQ ID NO: 1)-induced Drp1-Ser616 phosphorylation were evaluated. Cangelor inhibited Drp1-Ser616 phosphorylation with an IC50 of approximately 2 nM (FIG. 5B). SFLLRN (SEQ ID NO: 1)-induced Drp1-Ser616 phosphorylation was also sensitive to the FDA-approved antiplatelet drug cilostazol, which acts by inhibiting phosphodiesterase 3A (FIG. 2B). Lastly, the sensitivity of the assay for the most common antiplatelet therapeutic, aspirin, on the arachidonic acid-induced phosphorylation of Drp1-Ser616 was evaluated. Similar to the other antiplatelet therapies, a concentration dependent inhibition in phosphorylation at Ser616 in the presence of aspirin was observed with an IC50 of approximately 1 µM (FIG. 5C). Data indicate that inhibition of Drp1-Ser616 phosphorylation is a sensitive approach to detecting platelet inhibitors.

Figure 6A:
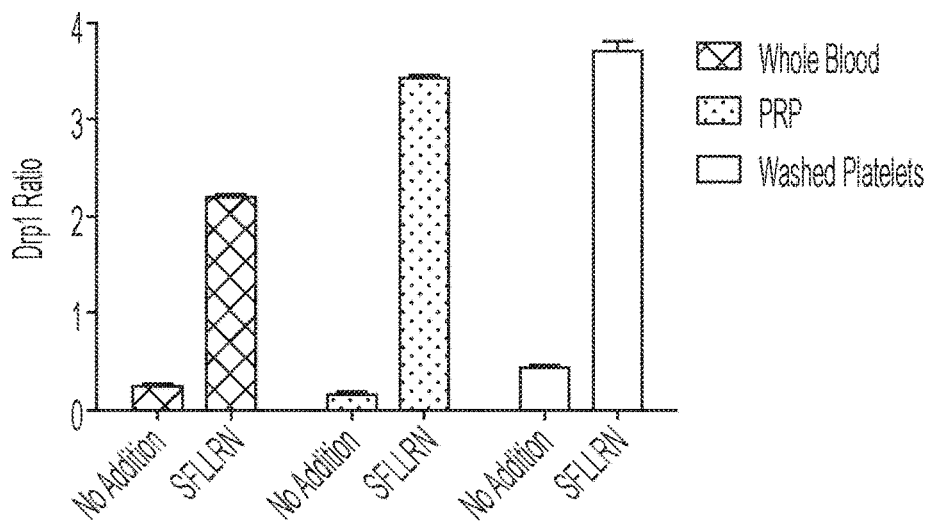
FIGS. 6A-6C show representative data for evaluation of Drp1-Ser616 phosphorylation in whole blood.
Figure 6B:
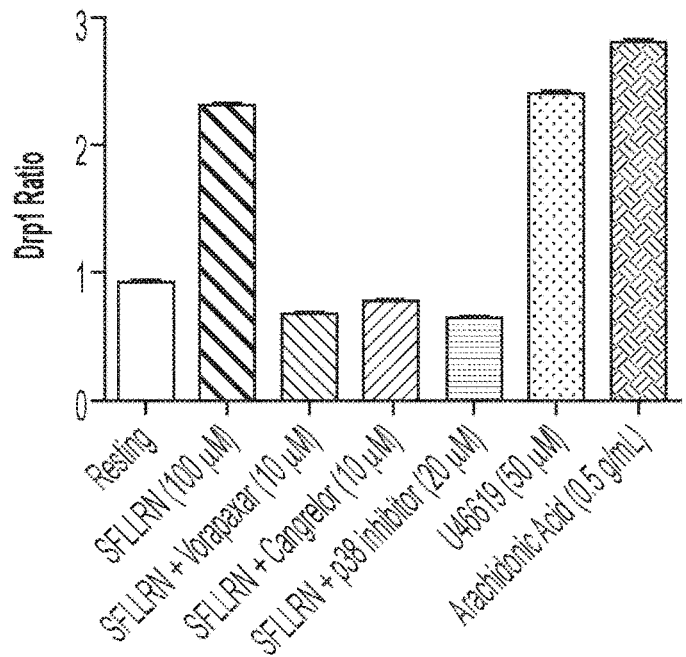
Figure 6C:
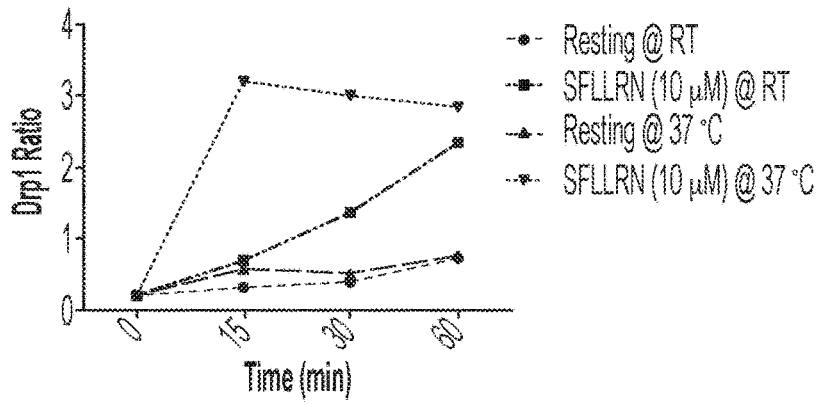

A point of care device designed to measure the effect of antiplatelet drugs on platelet signaling should be able to assay whole blood to enable rapid analysis. Since Drp1 is enriched in platelets and SFLLRN (SEQ ID NO: 1) stimulates through PAR1, which is also enriched in platelets, the Drp1-Ser616 phosphorylation assay could be compatible with whole blood. Drp1-Ser616 phosphorylation in whole blood samples was compared with platelet rich plasma (PRP) and washed platelets following stimulation with thrombin. Data indicated that while stimulation of washed platelets with thrombin provided the highest ratio of phospho-Drp1-Ser616 to total Drp1, both whole blood and platelet rich plasma also showed significant increases following thrombin stimulation (FIG. 6A). Since thrombin activates coagulation proteins in whole blood, SFLLRN (SEQ ID NO: 1) was used as an agonist in the whole blood assay. Stimulation of whole blood with SFLLRN (SEQ ID NO: 1) provided a greater than 2-fold increase in phospho-Drp1-Ser616 to total Drp1 (FIG. 6B). This signal was inhibited by vorapaxar, clopidogrel, and SB203580. Stimulation of whole blood with either the thromboxane prostanoid (TP) receptor agonist U46619 or arachidonic acid also resulted in significant stimulation of Drp1-Ser616 phosphorylation. Thus, data indicate that the Drp1 phosphorylation assay is compatible with whole blood.

The ability of the Drp1 phosphorylation assay to detect $P2Y_{12}$ inhibition in clinical samples was evaluated. Clopidogrel remains the most commonly used $P2Y_{12}$ antagonist. However, a substantial number of patients are reported to not metabolize clopidogrel into the active metabolite and therefore exhibit clopidogrel resistance. A modified Drp1-Ser616 phosphorylation assay was used to determine whether the assay is sensitive to $P2Y_{12}$ inhibition in patients receiving clopidogrel. The assay was compared to the gold standard, which is platelet aggregation, in a group of patient receiving both 75 mg clopidogrel and aspirin in preparation for carotid aneurysm surgery. Testing of $P2Y_{12}$ inhibition in clinical samples requires a positive control to ensure that the assay is working and that the platelet preparation is adequate. High dose thrombin was identified as an agonist that elicited Drp1-Ser616 phosphorylation even in the presence of $P2Y_{12}$ antagonism. The Drp1-Ser616 assay therefore included samples with both SFLLRN (SEQ ID NO: 1) (10 μM) and a high concentration of thrombin (1 U/ml) in order to overcome the requirement for ADP feedback. Using this approach, it was observed that both SFLLRN (SEQ ID NO: 1) and thrombin stimulated robust Drp1-Ser616 phosphorylation in untreated platelets, while only thrombin activated samples exhibited Drp1-Ser616 phosphorylation in the presence of clopidogrel (FIGS. 7A-7C). These results indicate the utility of using Drp1-Ser616 as a novel assay to assess antiplatelet therapies that work through inhibition of $P2Y_{12}$ or phosphodiesterases.

Example 3: Chemiluminescence Assay

Figure 9:
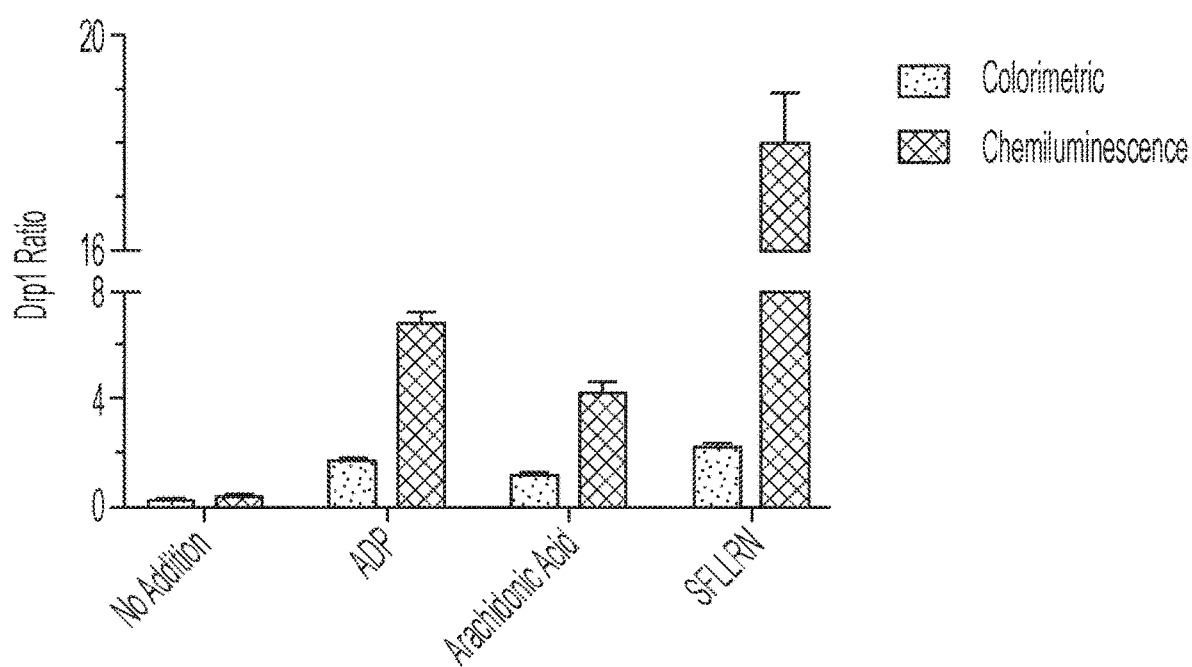
FIG. 9 shows a comparison between two formats of the Drp1 ratio assay including the colorimetric assay format and chemiluminescence assay format. Samples were activated with the indicated platelet agonists (ADP—20 µM; arachidonic acid—0.5 mg/mL; and SFLLRN (SEQ ID NO: 1)—25 µM) for 15 minutes at 37° C. Samples were subsequently lysed and assessed by either colorimetric or chemiluminescence ELISAs.

The suitability of the Drp1 phosphorylation assay for a chemiluminescence format was evaluated since this format is compatible with high throughput instrumentation available in clinical laboratories. A direct comparison of the chemiluminescence readout compared with the colorimetric readout showed increased signal in the chemiluminescence format in response to ADP, arachidonic acid, and SFLLRN (SEQ ID NO: 1) (FIG. 9).

Figure 10A:
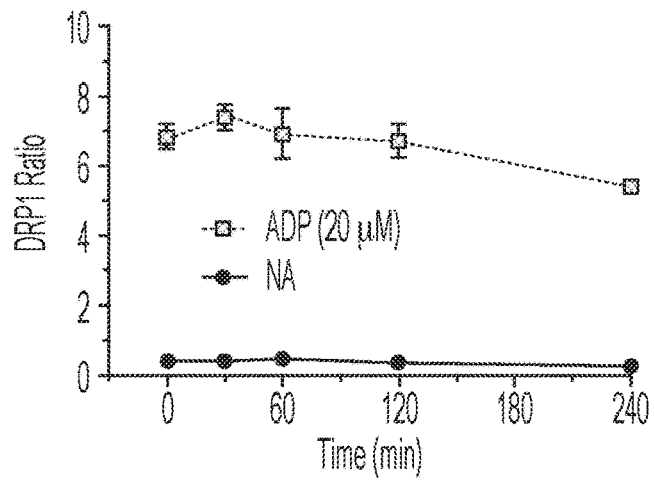
FIGS. 10A-10C show persistence of pDrp1 signal following stimulation of platelets. Samples were activated with the indicated platelet agonist [A: ADP (20 µM); B: arachidonic acid (500 µg/mL); and C: SFLLRN (SEQ ID NO: 1) (25 µM)] for 15 min at 37° C. and then lysed immediately. Samples were left at room temperature for the indicated amount of time prior to freezing (−80° C.) and were subsequently analyzed using the Drp1 ratio assay with a chemiluminescence format.
Figure 10B:
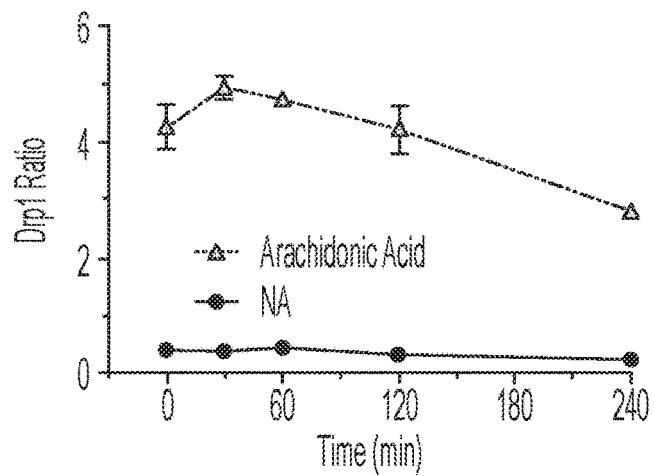
Figure 10C:
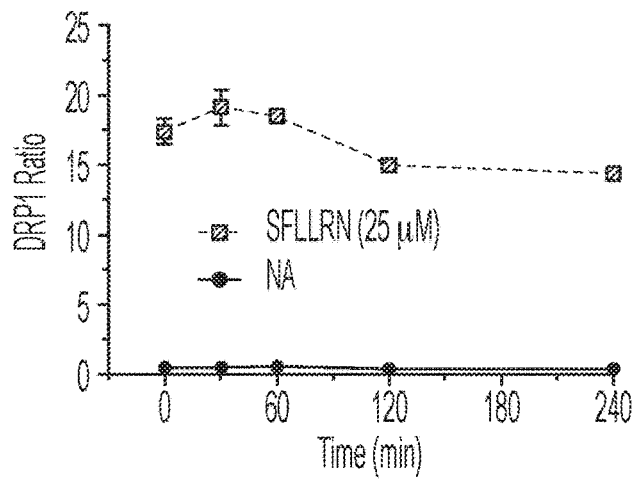

The stability of the phospho-Drp1-Ser616 signal is an important consideration, since some phosphorylation events are transient. For example, in the clinic, samples may not be assayed immediately following processing. Therefore, the stability of the Drp1 assay (FIGS. 10A-10C) was evaluated. The Drp1 ratio assay was stable over time, showing essentially no decrease in the Drp1 ratio after 120 mins when ADP or arachidonic acid were used as agonists (FIGS. 10A-10B), and less than a 15% decrease when SFLLRN (SEQ ID NO: 1) was used as an agonist (FIG. 10C). Even after 240 minutes, there was relatively little loss of signal.

Figure 11A:
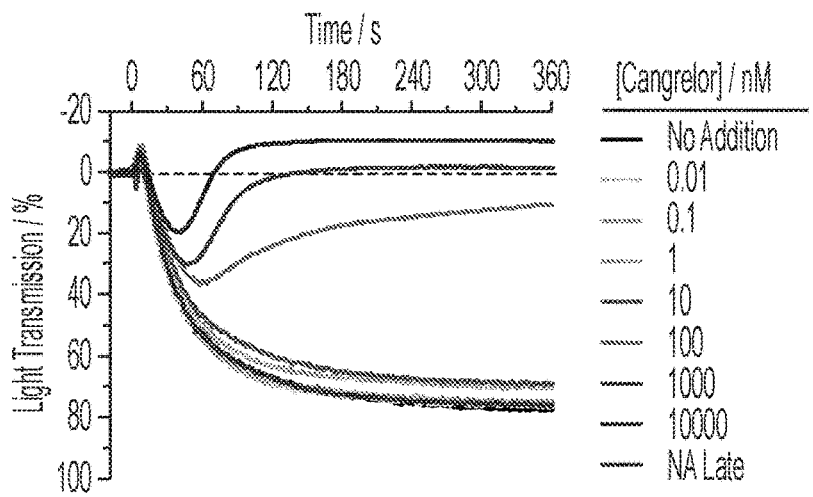
FIGS. 11A-11C shows a comparison of the Drp1 ratio assay to platelet aggregation. Cangrelor inhibition of platelet activation via ADP (20 µM) was evaluated using both aggregometry and the Drp1 ratio assay.
Figure 11B:
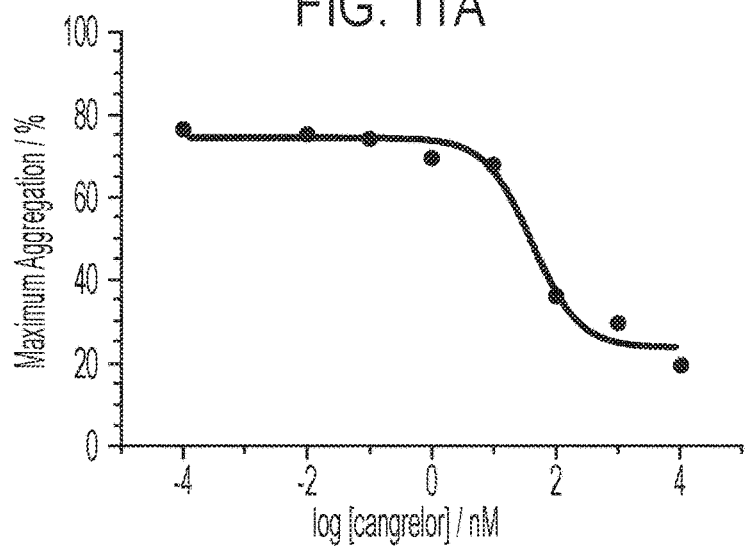
Figure 11C:
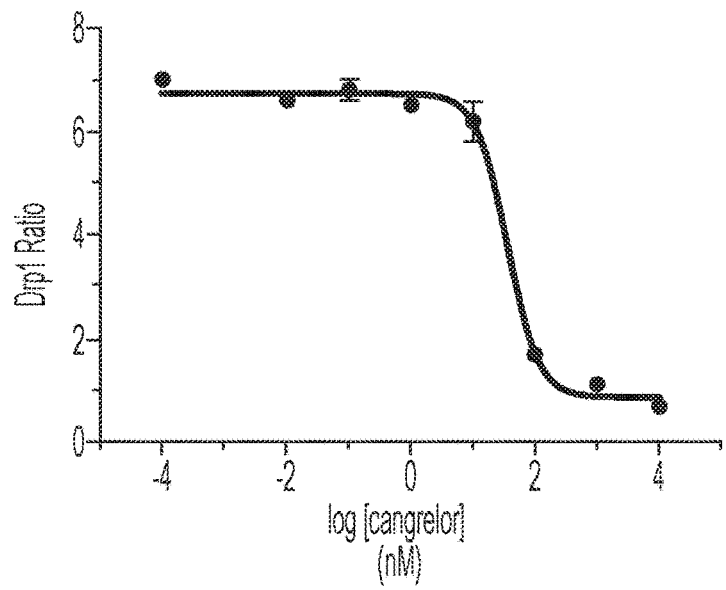

The sensitivity of the Drp1 ratio assay was compared with a platelet function test that is currently used in clinical laboratories by measuring platelet aggregation. Platelets were incubated with the indicated concentrations of the $P2Y_{12}$ inhibitor, cangrelor, and subsequently analyzed using both platelet aggregometry (FIGS. 11A-11B) and the Drp1 ratio assay (FIG. 11C). This analysis showed that platelet aggregometry and the Drp1 ratio assay were equally sensitive to inhibition by cangrelor.

Figure 12A:
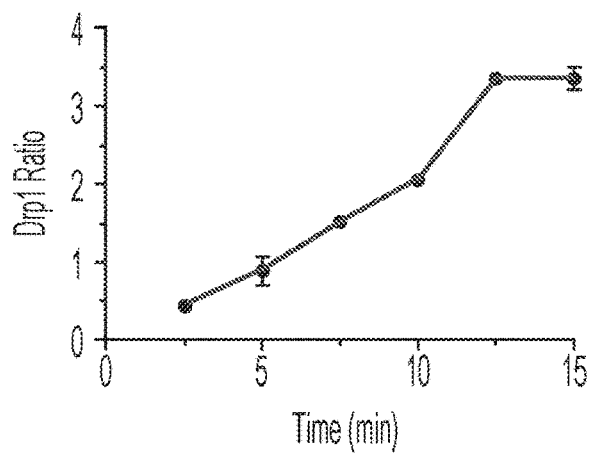
FIGS. 12A-12C show activation time studies with various platelet agonists. Platelets were exposed to agonists and subsequently analyzed using the Drp1 ratio assay with a chemiluminescence format.
Figure 12B:
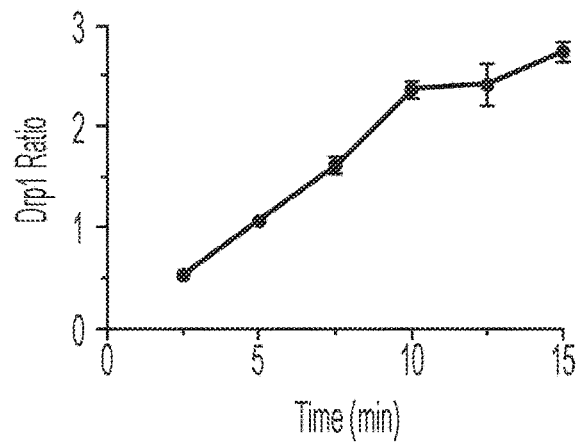
Figure 12C:
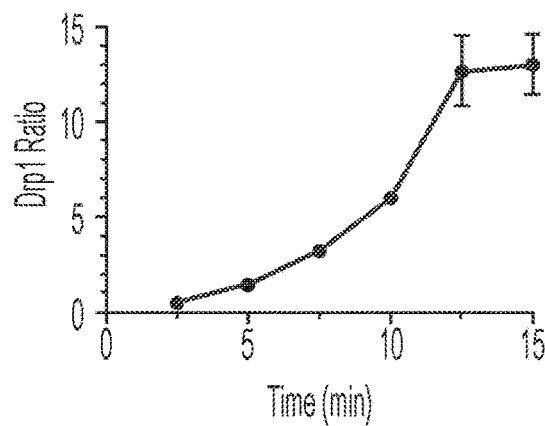

A time course of activation was performed to determine how long following exposure to agonist did it take for samples to reach maximum stimulation. This analysis showed that regardless of whether the samples were exposed to ADP (FIG. 12A), arachidonic acid (FIG. 12B), or SFLLRN (SEQ ID NO: 1) (FIG. 12C), the Drp1 ratio was elevated by 5 minutes and reached a maximum at approximately 12. 5 minutes.

What is claimed is:

1. A method comprising:
   (i) stimulating with a platelet agonist, a blood sample, platelet rich plasma sample, or purified platelet sample that has been obtained from a subject, wherein the platelet agonist is selected from arachidonic acid, protease-activated receptor 1 (PAR1) peptide agonists, protease-activated receptor 4 (PAR4) peptide agonists, adenosine diphosphate (ADP), and thromboxane (TP) receptor agonists;
   (ii) after stimulation, contacting the sample with an antibody that binds specifically to Dynamin-related protein 1 (Drp1) that is phosphorylated at position Ser616 (phospho-Drp1-Ser616), and a secondary reagent that binds to the antibody; and
   (iii) detecting the presence or absence of phospho-Drp1-Ser616, or a ratio of phospho-Drp1-Ser616: total Drp1, in the sample based upon the antibody binding to the phospho-Drp1-Ser616 and to the secondary reagent, wherein absence of phospho-Drp1-Ser616, or a phospho-Drp1-Ser616: total Drp1 ratio below 1.25, in the sample is indicative of the subject having been previously exposed to aspirin, vorapaxar, clopidogrel, cangrelor, prasugrel, ticagrelor, ticlopidine, cilostazol, a COX inhibitor, a non-steroidal anti-inflammatory (NSAID), terutroban, or dipyridamole.

2. The method of claim 1, wherein the antibody that binds specifically to phospho-Drp1-Ser616 does not bind to phospho-Drp1-Ser637.

3. The method of claim 1, wherein the secondary reagent is an antibody, single chain antibody (scFv), peptide or peptide fragment, or aptamer.

4. The method of claim 1, wherein the secondary reagent agent is conjugated to a detectable label.

5. The method of claim 4, wherein the detectable label is a polymeric particle, a metal particle, or a detectable moiety.

6. The method of claim 5, wherein the polymeric particle is a latex particle.

7. The method of claim 5, wherein the metal particle is a gold nanoparticle or magnetic nanoparticle.

8. The method of claim 5, wherein the detectable moiety is a fluorescent moiety, luminescent moiety, phosphorescent moiety, radiolabeled moiety, or a detectable enzyme.

9. The method of claim 1, wherein the PAR1 peptide agonist is a SFLLRN (SEQ ID NO: 1) peptide.

10. The method of claim 1, wherein the PAR4 agonist is a AYPGKF (SEQ ID NO: 2) peptide.

11. The method of claim 1, wherein the TP receptor agonist is U46619.

12. The method of claim 1, wherein the subject has or is suspected of having a cardiovascular disease or disorder or a cerebrovascular disease or disorder.

13. The method of claim 12, wherein the disease or disorder is selected from atherosclerotic disease, coronary artery disease, stable angina, coronary bypass surgery, stroke, thrombosis or thromboembolism, peripheral arterial disease, myocardial ischemia, myocardial infarction, atrial fibrillation (AF), aneurysm, pain, fever, inflammation, heparin-induced thrombocytopenia, Hermansky-Pudlak syndrome, Gray Platelet Syndrome, and impaired platelet function due to myelodysplastic syndrome.

14. The method of claim 1, wherein the subject is a human subject.

15. The method of claim 1, wherein the sample is a blood sample.

16. The method of claim 1, wherein the sample is a platelet rich plasma sample.

17. The method of claim 1, wherein the sample is a purified platelet sample.

\* \* \* \* \*

UNITED STATES PATENT AND TRADEMARK OFFICE
CERTIFICATE OF CORRECTION

| | |
|---|---|
| PATENT NO. | : 12,235,278 B2 |
| APPLICATION NO. | : 17/270830 |
| DATED | : February 25, 2025 |
| INVENTOR(S) | : Robert Flaumenhaft et al. |

It is certified that error appears in the above-identified patent and that said Letters Patent is hereby corrected as shown below:

On the Title Page

Item (57), ABSTRACT, please change the word:
"(Dip1)"
To:
--(Drp1)--

In the Claims

In Claim 4, at Column 24, Lines 54-55, please change the phrase:
"secondary reagent agent is"
To:
--secondary reagent is--

Signed and Sealed this
Thirteenth Day of May, 2025

Coke Morgan Stewart
*Acting Director of the United States Patent and Trademark Office*

SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

Ser Phe Leu Leu Arg Asn
1               5

<210> SEQ ID NO 2
<211> LENGTH: 6
<212> TYPE: PRT
<213> ORGANISM: Artificial Sequence
<220> FEATURE:

```
<223> OTHER INFORMATION: Synthetic Polypeptide

<400> SEQUENCE: 2

Ala Tyr Pro Gly Lys Phe
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is pyrrolysine

<400> SEQUENCE: 3

Leu Ile Gly Arg Leu Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 4

Leu Arg Gly Ile Leu Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

Thr Phe Leu Leu Arg
1               5
```